(12) United States Patent
Urch et al.

(10) Patent No.: US 11,440,900 B2
(45) Date of Patent: Sep. 13, 2022

(54) AGRICULTURAL CHEMICALS

(71) Applicant: GLOBACHEM NV, Sint-Truiden (BE)

(72) Inventors: Christopher John Urch, Alderley Edge (GB); Victoria Elizabeth Jackson, Alderley Edge (GB); Linda Jordan, Alderley Edge (GB); Effi Baetzner, Alderley Edge (GB); Oliver James Stephen McGaw, Alderley Edge (GB)

(73) Assignee: GLOBACHEM NV, Sint-Truiden (BE)

( * ) Notice: Subject to any disclaimer, the term of this patent is extended or adjusted under 35 U.S.C. 154(b) by 3 days.

(21) Appl. No.: 16/962,184

(22) PCT Filed: Jan. 15, 2019

(86) PCT No.: PCT/GB2019/050097
§ 371 (c)(1),
(2) Date: Jul. 14, 2020

(87) PCT Pub. No.: WO2019/141972
PCT Pub. Date: Jul. 25, 2019

(65) Prior Publication Data
US 2020/0339543 A1 Oct. 29, 2020

(30) Foreign Application Priority Data
Jan. 16, 2018 (GB) .................... 1800688

(51) Int. Cl.
| | |
|---|---|
| *C07D 403/04* | (2006.01) |
| *C07D 235/08* | (2006.01) |
| *C07D 249/18* | (2006.01) |
| *C07D 401/04* | (2006.01) |
| *A01N 43/52* | (2006.01) |
| *A01N 43/54* | (2006.01) |
| *A01N 43/58* | (2006.01) |
| *A01N 43/647* | (2006.01) |

(52) U.S. Cl.
CPC ........... *C07D 403/04* (2013.01); *A01N 43/52* (2013.01); *A01N 43/54* (2013.01); *A01N 43/58* (2013.01); *A01N 43/647* (2013.01); *C07D 235/08* (2013.01); *C07D 249/18* (2013.01); *C07D 401/04* (2013.01)

(58) Field of Classification Search
CPC .. C07D 235/08; C07D 249/18; C07D 401/04; C07D 403/04
See application file for complete search history.

(56) References Cited

FOREIGN PATENT DOCUMENTS

| | | |
|---|---|---|
| WO | 2005019207 A1 | 3/2005 |
| WO | 2009/000413 | 12/2008 |

OTHER PUBLICATIONS

Song et al. (J. Organometallic Chemistry 694 (2009) 1493-1502)—provided by Applicants in the IDS of Jul. 14, 2020.*
Diness, F. & Fairlie, D.P., "Catalyst-free N-arylation using unactivated fluorobenzenes," Angewandte Chemie International Edition, 2012, vol. 51, pp. 8012-8016.
Liu, L. et al., "Synthesis of chiral mono(N-heterocyclic carbene palladium and gold complexes with a 1,1'-biphenyl scaffold and their applications in catalysis," Beilstein Journal of Organic Chemistry, 2011, vol. 7, pp. 565-564.
Song, H. et al., "Synthesis and X-ray structures of rhodium complexes with new chiral biaryl-based NHC-ligands," Journal of Organometallic Chemistry, 2009, vol. 694, pp. 1493-1502.
Tao, S. et al., "Copper-catalyzed C—N bond exchange of N-heterocyclic substituents around pyridine and pyrimidine cores," Synthesis, 2017, vol. 49, pp. 5120-5130.
Search Report, dated Sep. 10, 2018, received in GB Application No. 1800688.2.
Al-Omran et al., "Synthesis of polyfunctionally substituted heteroaromatic compounds via benzotriazolyl chaicones with antimicrobial and antifungal activities," Journal of Heterocyclic Chemistry 41(3):327-333, May 1, 2004.
International Search Report and Written Opinion dated Apr. 4, 2019, Patent Application No. PCT/GB2019/050097, 14 pages.

* cited by examiner

*Primary Examiner* — Valerie Rodriguez-Garcia
(74) *Attorney, Agent, or Firm* — Davis Wright Tremaine LLP

(57) ABSTRACT

The present invention relates to benzimidazole and benzotriazole compounds which are of use in the field of agriculture as fungicides, wherein the compounds include benzimidazole and benzotriazole compounds having a structure according to formula 1, or an agronomically acceptable salt or N-oxide thereof:

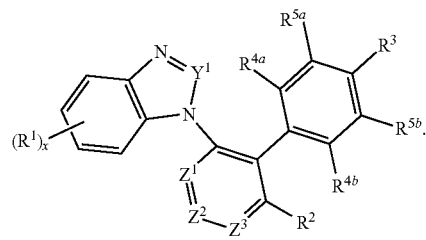

20 Claims, No Drawings

AGRICULTURAL CHEMICALS

CROSS-REFERENCE TO RELATED APPLICATIONS

The present application is a U.S. National Stage entry under 35 U.S.C. § 371 of International Application No. PCT/GB2019/050097, filed on Jan. 15, 2019, designating the United States of America and published in English on Jul. 25, 2019, which in turn claims priority to British Application No. GB 1800688.2, filed on Jan. 16, 2018, each of which is hereby incorporated by reference in its entirety.

The present invention relates to benzimidazole and benzotriazole compounds which are of use in the field of agriculture as fungicides.

Given the global increase in demand for food, there is an international need for new treatments to reduce food crop losses to disease, insects and weeds. Over 40% of crops are lost before harvest, and 10% post harvest, worldwide. Losses have actually increased since the mid-1990s.

A new threat contributing to this is the emergence of chemical-resistant organisms, for example, glyphosate-resistant weeds in USA and strobilurin-resistant strains of septoria fungal species.

Recent research also suggests that the geographical spread of many crop pests and diseases is increasing, possibly as a result of global warming.

An aim of certain embodiments of the present invention is to provide pesticides (e.g. fungicides) which have activity either non-selectively, i.e. broad spectrum activity, or which are active specifically against selective target organisms.

An aim of certain embodiments of the present invention is to provide compounds which are less persistent in the environment after use than prior art compounds. Alternatively or additionally the compounds of the present invention are less prone to bioaccumulation once in the food chain than prior art compounds.

Another aim of certain embodiments of the invention is to provide compounds which are less harmful to humans than prior art compounds. Alternatively or additionally, the compounds of the invention may be less harmful than prior art compounds to one or more of the following groups: amphibians, fish, mammals (including domesticated animals such as dogs, cats, cows, sheep, pigs, goats, etc.), reptiles, birds, and beneficial invertebrates (e.g. bees and other insects, or worms), beneficial nematodes, beneficial fungi and nitrogen-fixing bacteria.

The compounds of the invention may be as active as or more active than prior art compounds. They may have activity against organisms which have developed a resistance to prior art compounds. However, the present invention may also concern compounds which have only a low level activity relative to that of the prior art compounds. These lower activity compounds are still effective as fungicides but may have other advantages relative to existing compounds such as, for example, a reduced environmental impact.

The compounds of the invention may be more selective than prior art compounds, i.e. they may have better, similar or even slightly lower activity than prior art compound against target species but have a significantly lower activity against non-target species (e.g. the crops which are being protected).

Certain embodiments of the invention provide compounds that achieve one or more of the above aims. The compounds may be active in their own right or may metabolise or react in aqueous media to yield an active compound.

SUMMARY OF THE INVENTION

In a first aspect of the invention is provided a compound of formula I, or an agronomically acceptable salt or N-oxide thereof:

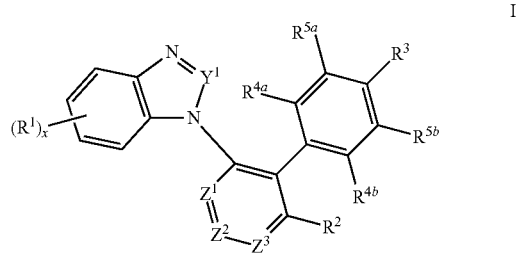

I $Y^1$ is selected from CH and N;

$Z^1$, $Z^2$ and $Z^3$ are each independently selected from N and $CR^6$; wherein at least one of $Z^1$, $Z^2$ and $Z^3$ is $CR^6$;

$R^1$ and $R^{10}$ are each independently at each occurrence selected from: $C_1$-$C_6$-alkyl, $C_1$-$C_6$-haloalkyl, $C_3$-$C_6$-cycloalkyl, halo, nitro, $OR^7$, $SR^8$, $OS(O)_2R^8$, $S(O)_2R^8$, $C(O)OR^8$, $C(O)NR^8R^8$, $C(O)R^8$, $S(O)_2NR^8R^8$, $S(O)(NR^8)R^8$, $S(O)R^8$, cyano, $C_2$-$C_6$-alkenyl, $C_2$-$C_6$-alkynyl, and $NR^8R^9$;

$R^2$ and $R^6$ are each independently at each occurrence selected from H, halo, nitro, cyano, $C_1$-$C_6$-alkyl, $C_3$-$C_6$-cycloalkyl and $C_1$-C6-haloalkyl;

$R^3$, $R^{4a}$, $R^{4b}$, $R^{5a}$ and $R^{5b}$ are independently at each occurrence selected from H, $C_1$-$C_6$-alkyl, $C_1$-$C_6$-haloalkyl, $C_3$-$C_6$-cycloalkyl, halo, nitro, $OR^7$, $SR^8$, $OS(O)_2R^8$, $S(O)_2R^8$, $C(O)OR^8$, $C(O)NR^8R^8$, $C(O)R^8$, $S(O)_2NR^8R^8$, $S(O)(NR^8)R^8$, $S(O)R^8$, cyano, $C_2$-$C_6$-alkenyl, $C_2$-$C_6$-alkynyl, and $NR^8R^9$; or wherein $R^{4b}$ and $R^{5b}$ together with the carbon atoms to which they are attached together form a ring selected from: phenyl, 5- or 6-membered heteroaryl, 5-, 6- or 7-membered heterocycloalkyl ring and $C_5$-$C_7$-cycloalkyl; said heteroaryl or phenyl ring being optionally substituted with from 1 to 4 $R^{10}$ groups or said heterocycloalkyl or cycloalkyl ring being optionally substituted with from 1 to 4 $R^{11}$ groups;

with the proviso that either at least one of $R^{4a}$ and $R^{4b}$ is selected from $C_1$-$C_6$-alkyl, $C_1$-$C_6$-haloalkyl, halo, nitro, O—$C_1$-$C_6$-alkyl, $SR^8$, $OS(O)_2R^8$, $S(O)_2R^8$, $S(O)_2NR^8R^8$, $S(O)(NR^8)R^8$, $S(O)R^8$, cyano, $C_2$-$C_6$-alkenyl, $C_2$-$C_6$-alkynyl, and $NR^8R^9$; or $R^{4b}$ and $R^{5b}$ together form a ring;

$R^7$ is independently at each occurrence selected from: H, $C_1$-$C_6$-alkyl, $C_3$-$C_6$-alkenyl, $C_3$-$C_6$-alkynyl, $C_3$-$C_6$-cycloalkyl and $C_1$-$C_6$-haloalkyl;

$R^8$ is independently at each occurrence selected from: H, $C_3$-$C_6$-cycloalkyl and $C_1$-$C_6$-alkyl;

or where two $R^8$ groups are attached to the same nitrogen atom, said $R^8$ groups, together with said nitrogen atom form a 4-, 5-, 6- or 7-membered heterocycloalkyl ring;

$R^9$ is independently at each occurrence selected from; H, $C_1$-$C_6$-alkyl, $C(O)$—$C_1$-$C_6$-alkyl and $S(O)_2$-$C_1$-$C_6$-alkyl;

or where an $R^8$ group and an $R^9$ group are attached to the same nitrogen atom, said $R^8$ and $R^9$ groups, together with said nitrogen atom form a 4-, 5-, 6- or 7-membered heterocycloalkyl ring;

$R^{11}$ is independently at each occurrence selected from: =O, =S, $C_1$-$C_6$-alkyl, $C_1$-$C_6$-haloalkyl, halo, nitro, $OR^8$, $SR^8$, $OS(O)_2R^8$, $S(O)_2R^8$, $S(O)_2NR^8R^8$, $S(O)(NR^8)R^8$, $S(O)R^8$, cyano, $C_2$-$C_6$-alkenyl, $C_2$-$C_6$-alkynyl, and $NR^8R^9$; and x is an integer from 0 to 4; wherein for any $R^1$, $R^2$, $R^3$, $R^{4a}$, $R^{4b}$, $R^{5a}$, $R^{5b}$, $R^6$, $R^7$, $R^8$, $R^9$, $R^{10}$, or $R^{11}$ group that is alkyl, alkenyl, cycloalkyl, heterocycloalkyl (including where two $R^8$ groups or an $R^8$ group and an $R^9$ group together with a nitrogen to which they are attached form a heterocycloalkyl ring), alkynyl, C(O)-alkyl or S(O)$_2$-alkyl is optionally substituted, where chemically possible, by 1 to 4 substituents which are each independently selected at each occurrence from the group consisting of: =O; =NR$^a$; =NOR$^a$, C$_1$-C$_4$-alkyl, halo, nitro, cyano, C$_1$-C$_4$-haloalkyl, C$_2$-C$_4$-alkenyl, C$_2$-C$_4$-alkynyl, NR$^a$R$^b$, S(O)$_2$R$^a$, S(O)R$^a$, S(O)(NR$^a$)R$^a$, S(O)$_2$NR$^a$R$^a$, CO$_2$R$^a$, C(O)R$^a$, CONR$^a$R$^a$ and OR$^a$;

wherein R$^a$ is independently selected from H and C$_1$-C$_4$-alkyl; and R$^b$ is independently H, C$_1$-C$_4$-alkyl, C(O)—C$_1$-C$_4$-alkyl, S(O)$_2$—C$_1$-C$_4$-alkyl.

In an embodiment, the compound of formula I is a compound of formula II:

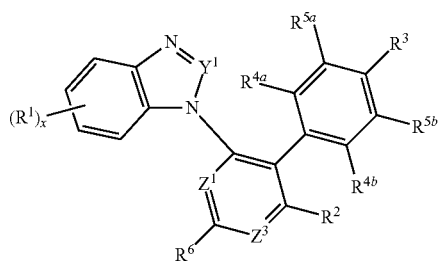

II wherein Y$^1$, Z$^1$, Z$^3$, R$^1$, R$^2$, R$^3$, R$^{4a}$, R$^{4b}$, R$^{5a}$, R$^{5b}$, R$^6$ and x are as described above for formula I. It may be that Y$^1$ is CH.

In an embodiment, the compound of formula I is a compound of formula III:

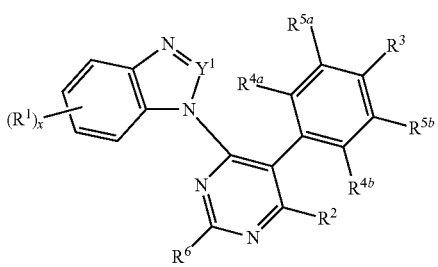

III wherein Y$^1$, R$^1$, R$^2$, R$^3$, R$^{4a}$, R$^{4b}$, R$^{5a}$, R$^{5b}$, R$^6$ and x are as described above for formula I. It may be that Y$^1$ is CH.

In an embodiment, the compound of formula I is a compound of formula IV:

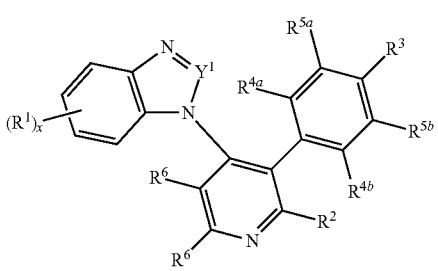

IV wherein Y$^1$, R$^1$, R$^2$, R$^3$, R$^{4a}$, R$^{4b}$, R$^{5a}$, R$^{5b}$, R$^6$ and x are as described above for formula I. It may be that Y$^1$ is CH.

In an embodiment, the compound of formula I is a compound of formula V:

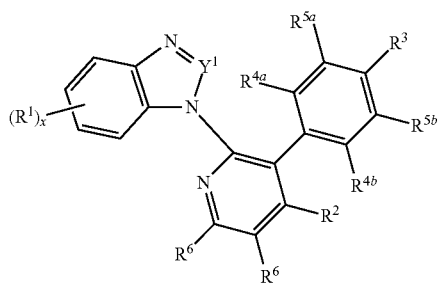

V wherein Y$^1$, R$^1$, R$^2$, R$^3$, R$^{4a}$, R$^{4b}$, R$^{5a}$, R$^{5b}$, R$^6$ and x are as described above for formula I. It may be that Y$^1$ is CH.

In an embodiment, the compound of formula I is a compound of formula VI:

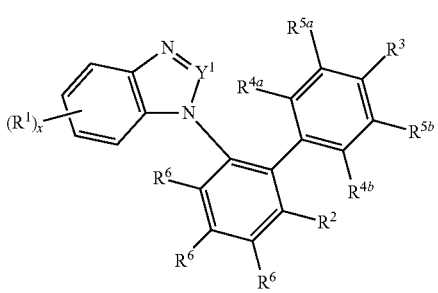

VI wherein Y$^1$, R$^1$, R$^2$, R$^3$, R$^{4a}$, R$^{4b}$, R$^{5a}$, R$^{5b}$, R$^6$ and x are as described above for formula I. It may be that Y$^1$ is CH.

In an embodiment, the compound of formula I is a compound of formula VII:

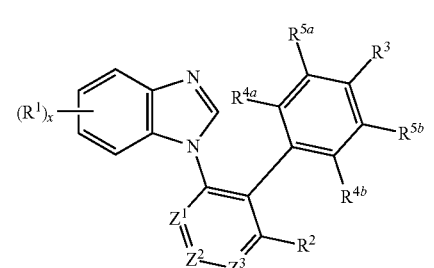

VI wherein Z$^1$, Z$^2$, Z$^3$, R$^1$, R$^2$, R$^3$, R$^{4a}$, R$^{4b}$, R$^{5a}$, R$^{5b}$ and x are as described above for formula I.

In an embodiment, the compound of formula I is a compound of formula VIII:

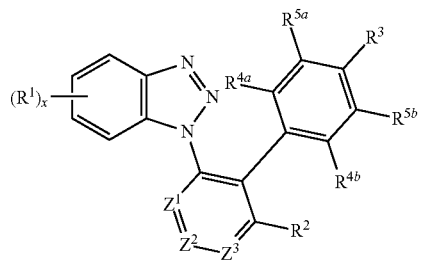

VIII wherein Z$^1$, Z$^2$, Z$^3$, R$^1$, R$^2$, R$^3$, R$^{4a}$, R$^{4b}$, R$^{5a}$, R$^{5b}$ and x are as described above for formula I.

The following embodiments apply to compounds of any of formulae (I)-(VIII). These embodiments are independent and interchangeable. Any one embodiment may be combined with any other embodiment, where chemically allowed. In other words, any of the features described in the following embodiments may (where chemically allowable) be combined with the features described in one or more other embodiments. In particular, where a compound is exemplified or illustrated in this specification, any two or more of the embodiments listed below, expressed at any level of generality, which encompass that compound may be combined to provide a further embodiment which forms part of the present disclosure.

It may be that $Y^1$ is CH. It may be that $Y^1$ is N.

It may be that $Z^2$ is $CR^6$.

It may be that $Z^1$ is N. It may be that $Z^1$ is $CR^6$.

It may be that $Z^3$ is N. It may be that $Z^3$ is $CR^6$.

It may be that $Z^1$ and $Z^3$ are each N and $Z^2$ is $CR^6$. It may be that $Z^1$ and $Z^2$ are each $CR^6$ and $Z^3$ is N. It may be that $Z^2$ and $Z^3$ are each $CR^6$ and $Z^1$ is N. It may be that $Z^1$, $Z^2$ and $Z^3$ are each $CR^6$.

It may be that x is an integer selected from 1 and 2.

It may be that $R^1$ is independently at each occurrence selected from $C_1$-$C_6$-alkyl, $C_1$-$C_6$-haloalkyl, halo, nitro, $OR^7$, and cyano. It may be that $R^1$ is independently at each occurrence selected from $C_1$-$C_6$-alkyl, $C_1$-$C_6$-haloalkyl, halo, nitro, $OR^7$, and cyano. It may be that $R^1$ is independently at each occurrence selected from halo, nitro, $OR^7$, and cyano. It may be that $R^1$ is independently at each occurrence $OR^7$ $R^1$ may be at at least one occurrence O—$C_3$-alkynyl, e.g. O-propargyl. $R^1$ may be at at least one occurrence O—$C_1$-$C_4$-alkyl, e.g. OMe. It may be that $R^1$ is independently at each occurrence halo, e.g. fluoro or chloro.

It may be that

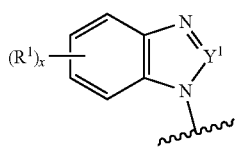

has the structure:

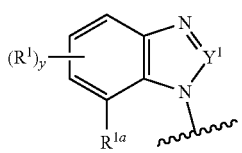

wherein y is an integer from 0 to 3; and wherein $R^{1a}$ is selected from halo and $OR^7$, e.g. OH, O—$C_1$-$C_4$-alkyl or O—$C_3$-alkynyl.

It may be that

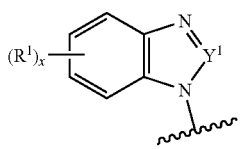

has the structure:

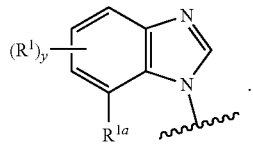

It may be that

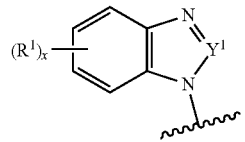

has the structure:

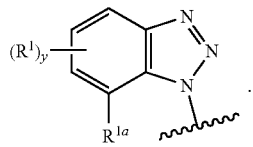

It may be that

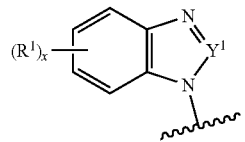

has the structure:

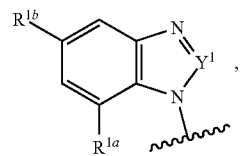

wherein $R^{1a}$ and $R^{1b}$ are each selected from halo and $OR^7$, e.g. OH, O—$C_1$-$C_4$-alkyl or O—$C_3$-alkynyl.

It may be that

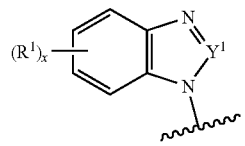

has the structure:

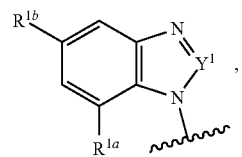

It may be that

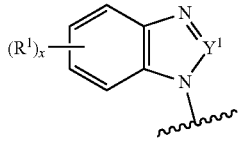

has the structure:

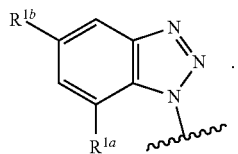

It may be that $R^{1a}$ is $OR^7$, e.g. OH, O—$C_1$-$C_4$-alkyl or O—$C_3$-alkynyl. It may be that $R^{1a}$ is O—$C_1$-$C_4$-alkyl, e.g. OMe. It may be that $R^{1a}$ is halo. It may be that $R^{1a}$ is fluoro.

It may be that $R^{1b}$ is $OR^7$, e.g. OH, O—$C_1$-$C_4$-alkyl or O—$C_3$-alkynyl. It may be that $R^{1b}$ is O—$C_1$-$C_4$-alkyl, e.g. OMe. It may be that $R^{1b}$ is halo, e.g. chloro or fluoro.

It may be that y is 0. It may be that y is 1.

In illustrative embodiments,

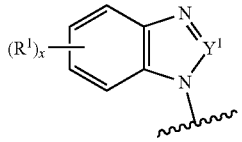

may have a structure selected from:

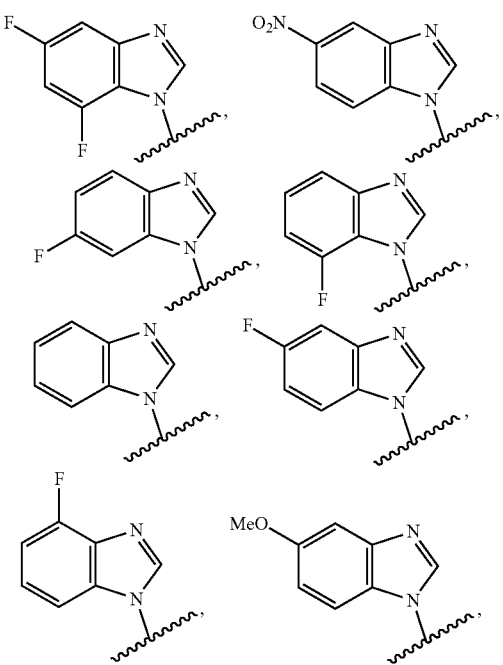

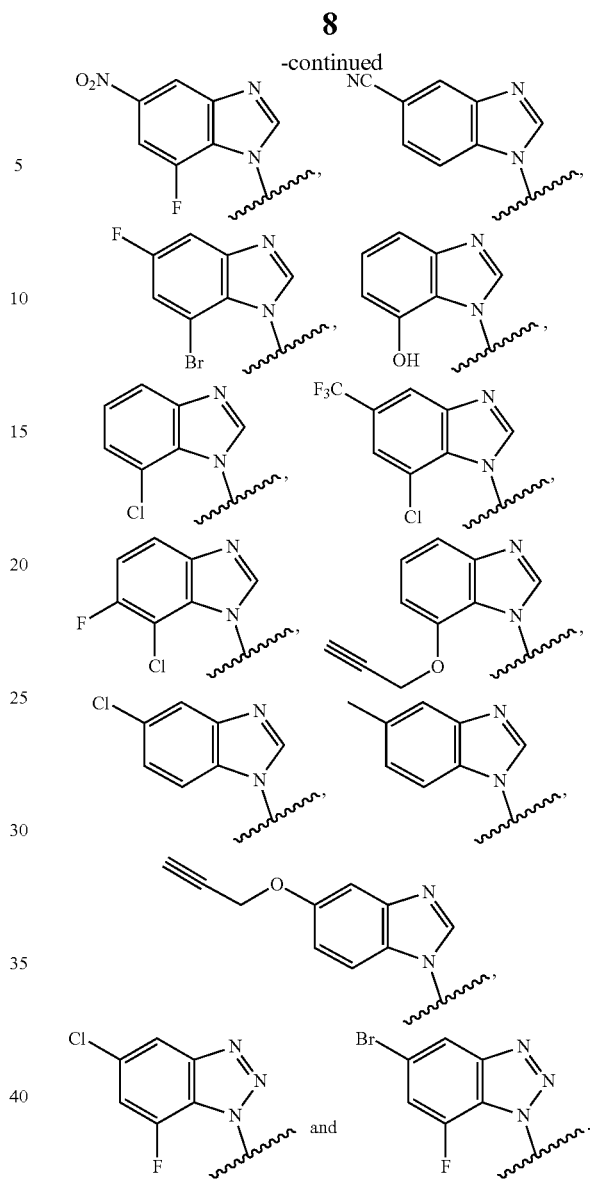

$R^2$ may be independently selected from halo, $C_1$-$C_2$-alkyl and $C_1$-$C_2$-haloalkyl. $R^2$ may be independently selected from chloro, $C_1$-$C_2$-alkyl and $C_1$-$C_2$-haloalkyl. $R^2$ may be independently selected from $C_1$-$C_2$-alkyl and $C_1$-$C_2$-haloalkyl. $R^2$ may be $C_1$-$C_2$-alkyl, e.g. methyl or ethyl. $R^2$ may be $C_1$-$C_2$-haloalkyl, e.g. $CF_3$. $R^2$ may be halo e.g. chloro.

It may be that $R^3$, $R^{4a}$, $R^{4b}$, $R^{5a}$ and $R^{5b}$ are each independently selected from H, halo, $C_1$-$C_6$-alkyl, $C_1$-$C_6$-haloalkyl, O—$C_1$-$C_6$-alkyl and O—$C_1$-$C_6$-haloalkyl.

It may be that $R^3$ is H. Alternatively, it may be that $R^3$ is independently selected from halo, $C_1$-$C_6$-alkyl, $C_1$-$C_6$-haloalkyl, O—$C_1$-$C_6$-alkyl and O—$C_1$-$C_6$-haloalkyl. It may be that $R^3$ is independently selected from halo, $C_1$-$C_6$-alkyl, $C_1$-$C_6$-haloalkyl, OH and O—$C_1$-$C_4$-alkyl. It may be that $R^3$ is halo e.g. fluoro or chloro. It may be that $R^3$ is O—$C_1$-$C_4$-alkyl e.g. OMe.

It may be that $R^{4a}$ is independently selected from halo, $C_1$-$C_6$-alkyl, $C_1$-$C_6$-haloalkyl, O—$C_1$-$C_6$-alkyl and O—$C_1$-$C_6$-haloalkyl. It may be that $R^{4a}$ is halo e.g. chloro.

It may be that $R^{4b}$ is H. Alternatively, it may be that $R^{4b}$ is independently selected from halo, $C_1$-$C_6$-alkyl, $C_1$-$C_6$-haloalkyl, O—$C_1$-$C_6$-alkyl and O—$C_1$-$C_6$-haloalkyl. It may be that $R^{4b}$ is halo e.g. chloro.

It may be that $R^{5a}$ is H. Alternatively, it may be that $R^{5a}$ is independently selected from halo, $C_1$-$C_6$-alkyl, $C_1$-$C_6$-haloalkyl, O—$C_1$-$C_6$-alkyl and O—$C_1$-$C_6$-haloalkyl.

It may be that neither $R^{4a}$ nor $R^{4b}$ are H.

It may be that both $R^{4a}$ and $R^{4b}$ are each independently selected from halo, $C_1$-$C_6$-alkyl, $C_1$-$C_6$-haloalkyl, O—$C_1$-$C_6$-alkyl and O—$C_1$-$C_6$-haloalkyl. It may be that both $R^{4a}$ and $R^{4b}$ are halo e.g. chloro.

It may be that $R^{5b}$ is H. Alternatively, it may be that $R^{5b}$ is independently selected from halo, $C_1$-$C_6$-alkyl, $C_1$-$C_6$-haloalkyl, O—$C_1$-$C_6$-alkyl and O—$C_1$-$C_6$-haloalkyl.

It may be that $R^{5a}$ and $R^{5b}$ are each H. It may be that $R^{4b}$ and $R^{5b}$ are each H. It may be that $R^{4b}$, $R^{5a}$ and $R^{5b}$ are each H.

It may be that none of $R^3$, $R^{4a}$ and $R^{4b}$ are H.

It may be that $R^3$, $R^{4a}$ and $R^{4b}$ are each independently selected from halo, $C_1$-$C_6$-alkyl, $C_1$-$C_6$-haloalkyl, O—$C_1$-$C_6$-alkyl and O—$C_1$-$C_6$-haloalkyl.

It may be that at least one of $R^{4a}$ and $R^{4b}$ is selected from $C_1$-$C_6$-alkyl, $C_1$-$C_6$-haloalkyl, chloro, bromo, iodo, nitro, O—$C_1$-$C_6$-alkyl, cyano, $C_2$-$C_6$-alkenyl and $C_2$-$C_6$-alkynyl. It may be that at least one of $R^{4a}$ and $R^{4b}$ is selected from $C_1$-$C_6$-alkyl, $C_1$-$C_6$-haloalkyl, chloro, bromo, iodo, O—$C_1$-$C_6$-alkyl, $C_2$-$C_6$-alkenyl and $C_2$-$C_6$-alkynyl.

The compound of formula (I) may be selected from:

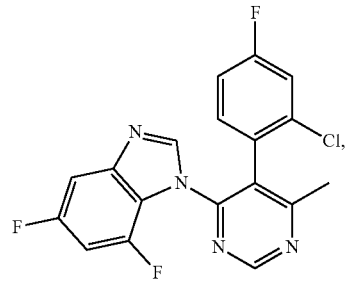

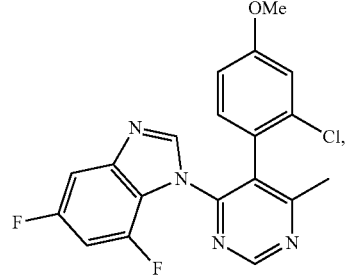

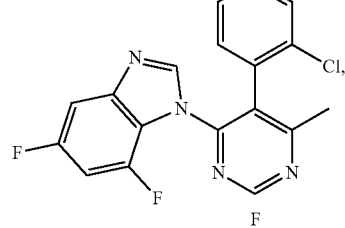

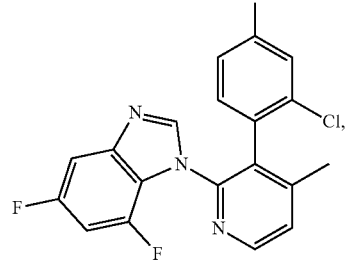

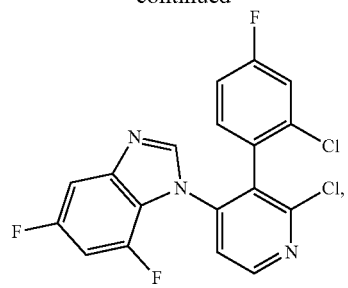

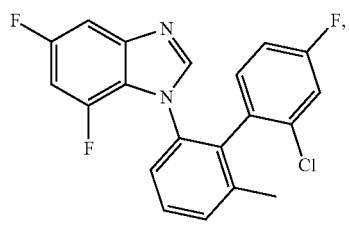

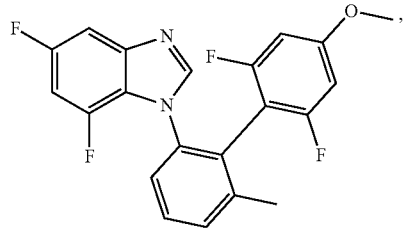

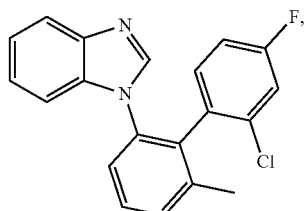

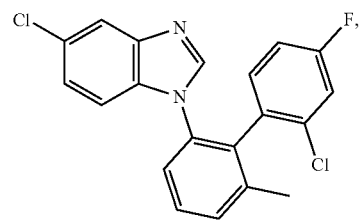

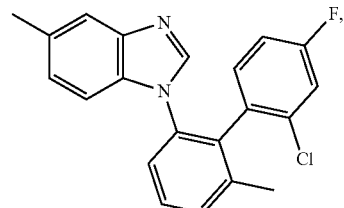

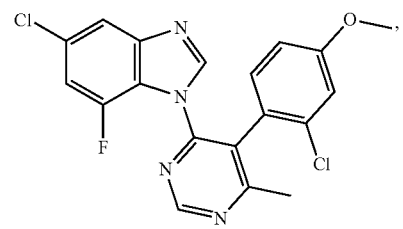

-continued
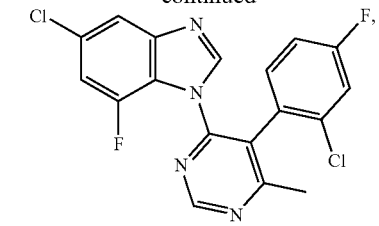
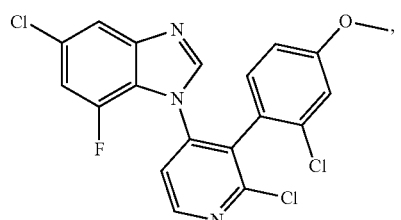
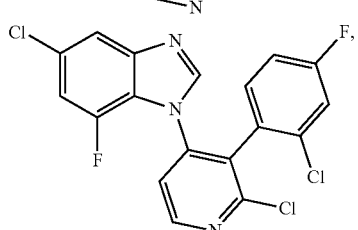
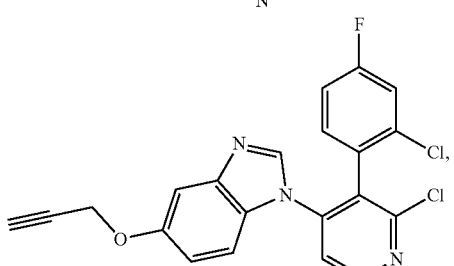
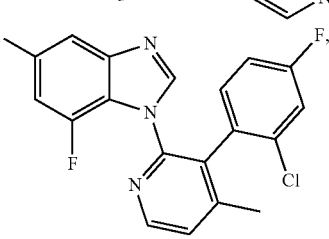
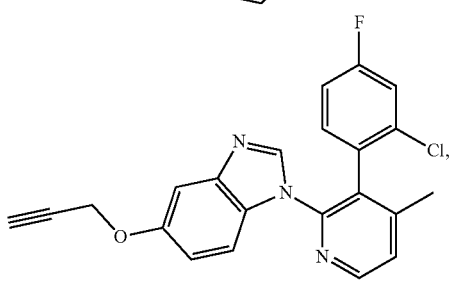
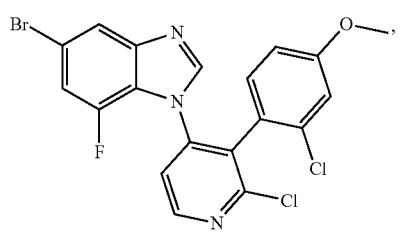
-continued
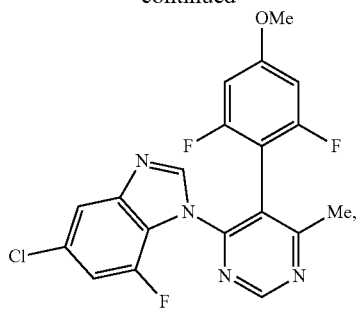
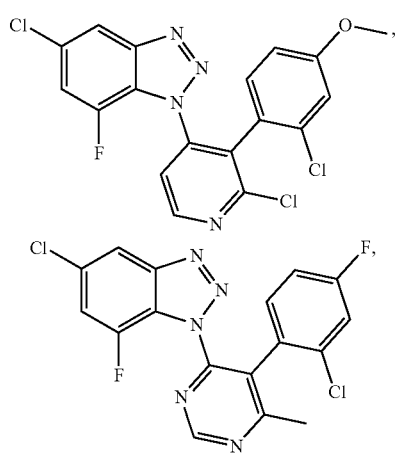
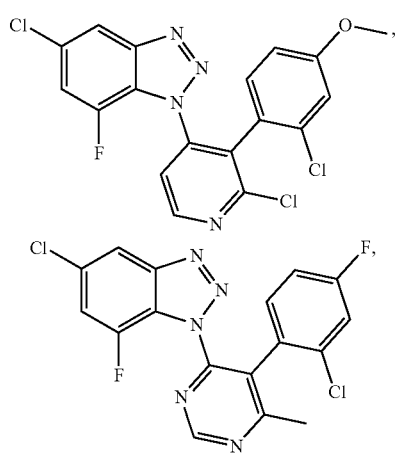
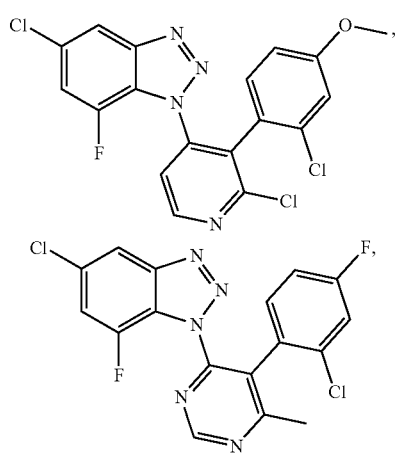
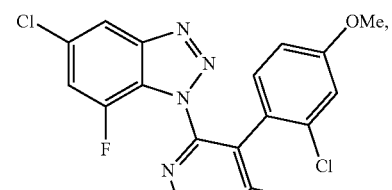
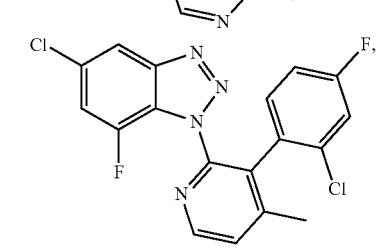
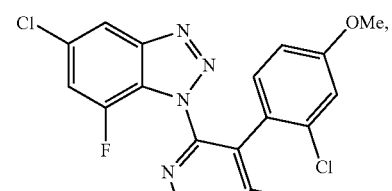
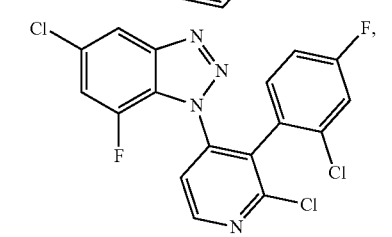

-continued

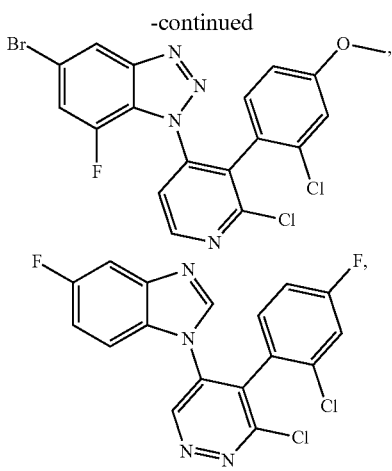

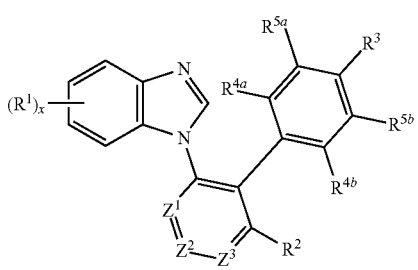

The invention may be as described in the following numbered paragraphs:

1. A compound of formula I, or an agronomically acceptable salt or N-oxide thereof:

I $Z^1$, $Z^2$ and $Z^3$ are each independently selected from N and $CR^6$; wherein at least one of $Z^1$, $Z^2$ and $Z^3$ is $CR^6$;

$R^1$ and $R^{10}$ are each independently at each occurrence selected from: $C_1$-$C_6$-alkyl, $C_1$-$C_6$-haloalkyl, $C_3$-$C_6$-cycloalkyl, halogen, nitro, $OR^7$, $SR^8$, $OS(O)_2R^8$, $S(O)_2R^8$, $C(O)OR^8$, $C(O)NR^8R^8$, $C(O)R^8$, $S(O)_2NR^8R^8$, $S(O)(NR^8)$ $R^8$, $S(O)R^8$, cyano, $C_2$-$C_6$-alkenyl, $C_2$-$C_6$-alkynyl, and $NR^8R^9$;

$R^2$ and $R^6$ are each independently at each occurrence selected from H, halo, nitro, cyano, $C_1$-$C_6$-alkyl, $C_3$-$C_6$-cycloalkyl and $C_1$-$C_6$-haloalkyl;

$R^3$, $R^{4a}$, $R^{4b}$, $R^{5a}$ and $R^{5b}$ are independently at each occurrence selected from H, $C_1$-$C_6$-alkyl, $C_1$-$C_6$-haloalkyl, $C_3$-$C_6$-cycloalkyl, halogen, nitro, $OR^7$, $SR^8$, $OS(O)_2R^8$, $S(O)_2R^8$, $C(O)OR^8$, $C(O)NR^8R^8$, $C(O)R^8$, $S(O)_2NR^8R^8$, $S(O)(NR^8)R^8$, $S(O)R^8$, cyano, $C_2$-$C_6$-alkenyl, $C_2$-$C_6$-alkynyl, and $NR^8R^9$; or wherein $R^{4b}$ and $R^{5b}$ together with the carbon atoms to which they are attached together form a ring selected from: phenyl, 5- or 6-membered heteroaryl, 5-, 6- or 7-membered heterocycloalkyl ring and $C_5$-$C_7$-cycloalkyl; said heteroaryl or phenyl ring being optionally substituted with from 1 to 4 $R^{10}$ groups or said heterocycloalkyl or cycloalkyl ring being optionally substituted with from 1 to 4 $R^{11}$ groups;

with the proviso that either at least one of $R^{4a}$ and $R^{4b}$ is selected from $C_1$-$C_6$-alkyl, $C_1$-$C_6$-haloalkyl, halo, nitro, O—$C_1$-$C_6$-alkyl, $SR^8$, $OS(O)_2R^8$, $S(O)_2R^8$, $S(O)_2NR^8R^8$, $S(O)(NR^8)R^8$, $S(O)R^8$, cyano, $C_2$-$C_6$-alkenyl, $C_2$-$C_6$-alkynyl, and $NR^8R^9$; or $R^{4b}$ and $R^{5b}$ together form a ring;

$R^7$ is independently at each occurrence selected from: H, $C_1$-$C_6$-alkyl, $C_3$-$C_6$-alkenyl, $C_3$-$C_6$-alkynyl, $C_3$-$C_6$-cycloalkyl and $C_1$-$C_6$-haloalkyl;

$R^8$ is independently at each occurrence selected from: H, $C_3$-$C_6$-cycloalkyl and $C_1$-$C_6$-alkyl;

or where two $R^8$ groups are attached to the same nitrogen atom, said $R^8$ groups, together with said nitrogen atom form a 4-, 5-, 6- or 7-membered heterocycloalkyl ring;

$R^9$ is independently at each occurrence selected from; H, $C_1$-$C_6$-alkyl, C(O)—$C_1$-$C_6$-alkyl and $S(O)_2$—$C_1$-$C_6$-alkyl;

or where an $R^8$ group and an $R^9$ group are attached to the same nitrogen atom, said $R^8$ and $R^9$ groups, together with said nitrogen atom form a 4-, 5-, 6- or 7-membered heterocycloalkyl ring;

$R^{11}$ is independently at each occurrence selected from: =O, =S, $C_1$-$C_6$-alkyl, $C_1$-$C_6$-haloalkyl, halogen, nitro, $OR^8$, $SR^8$, $OS(O)_2R^8$, $S(O)_2R^8$, $S(O)_2NR^8R^8$, $S(O)(NR^8)R^8$, $S(O)R^8$, cyano, $C_2$-$C_6$-alkenyl, $C_2$-$C_6$-alkynyl, and $NR^8R^9$; and x is an integer from 0 to 4;

wherein for any $R^1$, $R^2$, $R^3$, $R^{4a}$, $R^{4b}$, $R^{5a}$, $R^{5b}$, $R^6$, $R^7$, $R^8$, $R^9$, $R^{10}$, or $R^{11}$ group that is alkyl alkenyl, cycloalkyl, heterocycloalkyl (including where two $R^8$ groups or an $R^8$ group and an $R^9$ group together with a nitrogen to which they are attached form a heterocycloalkyl ring), alkynyl, C(O)-alkyl or $S(O)_2$-alkyl is optionally substituted, where chemically possible, by 1 to 4 substituents which are each independently selected at each occurrence from the group consisting of: =O; =$NR^a$, =$NOR^a$, $C_1$-$C_4$-alkyl, halo, nitro, cyano, $C_1$-$C_4$-haloalkyl, $C_2$-$C_4$-alkenyl, $C_2$-$C_4$-alkynyl, $NR^aR^b$, $S(O)_2R^a$, $S(O)R^a$, $S(O)(NR^a)R^a$, $S(O)_2NR^aR^a$, $CO_2R^a$, $C(O)R^a$, $CONR^aR^a$ and $OR^a$;

wherein $R^a$ is independently selected from H and $C_1$-$C_4$-alkyl; and $R^b$ is independently H, $C_1$-$C_4$-alkyl, C(O)—$C_1$-$C_4$-alkyl, $S(O)_2$—$C_1$-$C_4$-alkyl.

2. A compound of paragraph 1, wherein $Z^2$ is $CR^6$.

3. A compound of paragraph 1 or paragraph 2, wherein $Z^1$ and $Z^3$ are each N.

4. A compound of paragraph 1 or paragraph 2, wherein $Z^1$ is $CR^6$ and $Z^3$ is N.

5. A compound of paragraph 1 or paragraph 2, wherein $Z^3$ is $CR^6$ and $Z^1$ is N.

6. A compound of paragraph 1 or paragraph 2, wherein $Z^1$ and $Z^3$ are each $CR^6$.

7. A compound of any one of paragraphs 1 to 6, wherein x is an integer selected from 1 and 2 and $R^1$ is independently at each occurrence selected from $C_1$-$C_4$-alkyl, $C_1$-$C_4$-haloalkyl, halogen, nitro, $OR^8$, and cyano.

8. A compound of any one of paragraphs 1 to 7, wherein $R^2$ is independently selected from $C_1$-$C_2$-alkyl and $C_1$-$C_2$-haloalkyl.

9. A compound of any one of paragraphs 1 to 8, wherein $R^{4a}$ is independently selected from halo, $C_1$-$C_4$-alkyl, $C_1$-$C_4$-haloalkyl, O—$C_1$-$C_4$-alkyl and O—$C_1$-$C_4$-haloalkyl.

10. A compound of any one of paragraphs 1 to 9, wherein $R^{4b}$ is independently selected from halo, $C_1$-$C_4$-alkyl, $C_1$-$C_4$-haloalkyl, O—$C_1$-$C_4$-alkyl and O—$C_1$-$C_4$-haloalkyl.

11. A compound of any one of paragraphs 1 to 10, wherein neither $R^{4a}$ nor $R^{4b}$ are H.

12. A compound of any one of paragraphs 1 to 9, wherein $R^{4b}$ is H.

13. A compound of any one of paragraphs 1 to 12, wherein $R^{5a}$ is H.

14. A compound of any one of paragraphs 1 to 13, wherein $R^{5b}$ is H.

15. A compound of any one of paragraphs 1 to 14, wherein $R^3$ is independently selected from halo, $C_1$-$C_4$-alkyl, $C_1$-$C_4$-haloalkyl, O—$C_1$-$C_4$-alkyl and O—$C_1$-$C_4$-haloalkyl.

16. A method for controlling fungal diseases, the method comprising applying an agronomically effective and substantially non-phytotoxic quantity of a compound of any one of paragraphs 1 to 16 to seeds of plants, to plants themselves or to an area where it is intended that plants will grow.

17. A use of a compound of any one of paragraphs 1 to 16 to control fungal diseases of plants.

18. A fungicidal composition comprising an effective and non-phytotoxic amount of an active compound of any one of paragraphs 1 to 16.

DETAILED DESCRIPTION

The term $C_m$-$C_n$ refers to a group with m to n carbon atoms.

The term "alkyl" refers to a linear or branched saturated monovalent hydrocarbon chain. For example, $C_1C_6$-alkyl may refer to methyl, ethyl, n-propyl, iso-propyl, n-butyl, sec-butyl, tert-butyl, n-pentyl or n-hexyl. The alkyl groups may be unsubstituted or substituted by one or more substituents. Specific substituents for each alkyl group independently may be fluorine, $OR^a$ or $NHR^a$.

The term "haloalkyl" refers to a hydrocarbon group substituted with at least one halogen atom independently chosen at each occurrence from: fluorine, chlorine, bromine and iodine. The halogen atom may be present at any position on the hydrocarbon chain. For example, $C_1$-$C_6$-haloalkyl may refer to chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoroethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl. A haloalkyl group may be a fluoroalkyl group, i.e. a hydrocarbon chain substituted with at least one fluorine atom. Thus, a haloalkyl group may have any amount of halogen substituents. The group may contain a single halogen substituent, it may have two or three halogen substituents, or it may be saturated with halogen substituents.

The term "alkenyl" refers to a branched or linear hydrocarbon group containing at least one double bond. The double bond(s) may be present as the E or Z isomer. The double bond may be at any possible position of the hydrocarbon chain. For example, "$C_2$-$C_6$-alkenyl" may refer to ethenyl, propenyl, butenyl, butadienyl, pentenyl, pentadienyl, hexenyl and hexadienyl. The alkenyl groups may be unsubstituted or substituted by one or more substituents. Specific substituents for any saturated carbon atom in each alkenyl group independently may be fluorine, $OR^a$ or $NHR^a$.

The term "alkynyl" refers to a branched or linear hydrocarbon chain containing at least one triple bond. The triple bond may be at any possible position of the hydrocarbon chain. For example, "$C_2$-$C_6$-alkynyl" may refer to ethynyl, propynyl, butynyl, pentynyl and hexynyl. The alkynyl groups may be unsubstituted or substituted by one or more substituents. Specific substituents for any saturated carbon atom in each alkynyl group independently may be fluorine, $OR^a$ or $NHR^a$.

The term "cycloalkyl" refers to a saturated hydrocarbon ring system containing, for example, 3, 4, 5 or 6 carbon atoms. For example, "$C_3$-$C_6$-cycloalkyl" may refer to cyclopropyl, cyclobutyl, cyclopentyl, cyclohexyl. The cycloalkyl groups may be unsubstituted or substituted by one or more substituents. Specific substituents for each cycloalkyl group independently may be fluorine, $OR^a$ or $NHR^a$.

The term heterocycloalkyl may refer to a monocyclic or bicyclic saturated or partially saturated group having the indicated number of atoms in the ring system and comprising 1 or 2 heteroatoms independently selected from O, S and N in the ring system (in other words 1 or 2 of the atoms forming the ring system are selected from O, S and N). By partially saturated it is meant that the ring may comprise one or two double bonds. This applies particularly to monocyclic rings with from 5 to 6 members. The double bond will typically be between two carbon atoms but may be between a carbon atom and a nitrogen atom. Examples of heterocycloalkyl groups include; piperidine, piperazine, morpholine, thiomorpholine, pyrrolidine, tetrahydrofuran, tetrahydrothiophene, dihydrofuran, tetrahydropyran, dihydropyran, dioxane and azepine. A heterocycloalkyl group may be unsubstituted or substituted by one or more substituents. Specific substituents for any saturated carbon atom in each heterocycloalkyl group may independently be fluorine, $OR^a$ or $NHR^a$.

Aryl groups may be any aromatic carbocyclic ring system (i.e. a ring system containing $2(2n+1)\pi$ electrons). Aryl groups may have from 6 to 12 carbon atoms in the ring system. Aryl groups will typically be phenyl groups. Aryl groups may be naphthyl groups or biphenyl groups.

In any of the above aspects and embodiments, heteroaryl groups may be any aromatic (i.e. a ring system containing $2(2n+1)\pi$ electrons) 5-10 membered ring system comprising from 1 to 4 heteroatoms independently selected from O, S and N (in other words from 1 to 4 of the atoms forming the ring system are selected from O, S and N). Thus, any heteroaryl groups may be independently selected from: 5 membered heteroaryl groups in which the heteroaromatic ring is substituted with 1-4 heteroatoms independently selected from O, S and N; and 6-membered heteroaryl groups in which the heteroaromatic ring is substituted with 1-3 (e.g.1-2) nitrogen atoms; 9-membered bicyclic heteroaryl groups in which the heteroaromatic system is substituted with 1-4 heteroatoms independently selected from O, S and N; 10-membered bicyclic heteroaryl groups in which the heteroaromatic system is substituted with 1-4 nitrogen atoms. Specifically, heteroaryl groups may be independently selected from: pyrrole, furan, thiophene, pyrazole, imidazole, oxazole, isoxazole, triazole, oxadiazole, thiadiazole, tetrazole; pyridine, pyridazine, pyrimidine, pyrazine, triazine, indole, isoindole, benzofuran, isobenzofuran, benzothiophene, indazole, benzimidazole, benzoxazole, benzthiazole, benzisoxazole, purine, quinoline, isoquinoline, cinnoline, quinazoline, quinoxaline, pteridine, phthalazine and naphthyridine.

It may be that, in any group which is an aryl or heteroaryl group, that aryl or heteroaryl group is unsubstituted or is optionally substituted, where chemically possible, by 1 to 5 substituents which are each independently selected at each occurrence from: halo, nitro, cyano, $NR^aR^a$, $NR^aS(O)_2R^a$, $NR^aC(O)R^a$, $NR^aCONR^aR^a$, $NR^aCO_2R^a$, $OR^a$, $SR^a$, $S(O)R^a$, $S(O)_2OR^a$, $S(O)_2R^a$, $S(O)_2NR^aR^a$, $CO_2R^aC(O)R^a$, $CONR^aR^a$, $CR^bR^bNR^aR^a$, $CR^bR^bOR^a$, $C_1$-$C_4$-alkyl, $C_2$-$C_4$-alkenyl, $C_2$-$C_4$-alkynyl and $C_1$-$C_4$-haloalkyl; wherein $R^a$ and $R^b$ are as described above for formula I.

Compounds of the invention containing one or more asymmetric carbon atoms can exist as two or more stereoisomers (e.g. enantiomers or diastereoisomers).

Where a compound of the invention contains a double bond such as a C=C or C=N group, geometric cis/trans (or Z/E) isomers are possible. Where structural isomers are interconvertible via a low energy barrier, tautomeric isomerism ('tautomerism') can occur. This can take the form of proton tautomerism in compounds of the invention containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of the invention, including compounds exhibiting more than one type of isomerism, and mixtures of one or more thereof.

The compounds of the invention may be obtained, stored and/or used in the form of an agronomically acceptable salt. Suitable salts include, but are not limited to, salts of acceptable inorganic acids such as hydrochloric, sulfuric, phosphoric, nitric, carbonic, boric, sulfamic, and hydrobromic acids, or salts of agronomically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulfonic, toluenesulfonic, benzenesulfonic, salicylic, sulfanilic, aspartic, glutamic, edetic, stearic, palmitic, oleic, lauric, pantothenic, tannic, ascorbic and valeric acids. Suitable salts also include salts of inorganic and organic bases, e.g. counterions such as Na, Ca, K, Li, Mg, ammonium, trimethylsulfonium. The compounds may also be obtained, stored and/or used in the form of an N-oxide. Also included are acid addition salts or base salts wherein the counter ion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers when necessary include chiral synthesis from a suitable optically pure precursor or resolution of the racemate (or the racemate of a salt or derivative) using, for example, chiral high pressure liquid chromatography (HPLC). Thus, chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and for specific examples, 0 to 5% by volume of an alkylamine e.g. 0.1% diethylamine. Concentration of the eluate affords the enriched mixture.

Alternatively, the racemate (or a racemic precursor) may be reacted with a suitable optically active compound, for example, an alcohol, or, in the case where the compound of the invention contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer. While both of the crystal forms present in a racemic mixture have identical physical properties, they may have different physical properties compared to the true racemate.

Racemic mixtures may be separated by conventional techniques known to those skilled in the art—see, for example, "Stereochemistry of Organic Compounds" by E. L. Eliel and S. H. Wilen (Wiley, 1994).

The activity of the compounds of the present invention can be assessed by a variety of in silico, in vitro and in vivo assays. In silico analysis of a variety of compounds has been demonstrated to be predictive of ultimate in vitro and even in vivo activity.

The present invention also includes all environmentally acceptable isotopically-labelled compounds of formulae I to VIII and their syntheses, wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$.

Isotopically-labelled compounds can generally be prepared by conventional techniques known to those skilled in the art or by processes analogous to those described using an appropriate isotopically-labelled reagent in place of the non-labelled reagent previously employed.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

If appropriate, the compounds of the invention can, at certain concentrations or application rates, be used as fungicides.

According to another aspect of the present invention, there is provided a method for controlling fungal diseases, the method comprising applying an agronomically effective and substantially non-phytotoxic (to the crop plant) quantity of a compound of the invention to the seeds of the plants, to the plants themselves or to the area where it is intended that the plants will grow.

The pesticide may be applied as a seed treatment, foliar application, stem application, drench or drip application (chemigation) to the seed, the plant or to the fruit of the plant or to soil or to inert substrate (e.g. inorganic substrates like sand, rockwool, glasswool; expanded minerals like perlite, vermiculite, zeolite or expanded clay), Pumbe, Pyroclastic materials or stuff, synthetic organic substrates (e.g. polyurethane) organic substrates (e.g. peat, composts, tree waste products like coir, wood fibre or chips, tree bark) or to a liquid substrate (e.g. floating hydroponic systems, Nutrient Film Technique, Aeroponics).

In a further aspect, the present invention also relates to a fungicidal composition comprising an effective and non-phytotoxic amount of an active compound of the invention. The composition may further comprise one or more additional fungicides.

The term "effective and non-phytotoxic amount" means an amount of pesticide according to the invention which is sufficient to control or destroy any of the targeted pests present or liable to appear in the crops and which does not have any significant detrimental effect on the crops or indeed has a positive effect on plant vigour and yield in the absence of target organism.

The amount will vary depending on the pest to be controlled, the type of crop, the climatic conditions and the compounds included in the pesticidal composition. This amount can be determined by systematic field trials, which are within the capabilities of a person skilled in the art.

Depending on their particular physical and/or chemical properties, the active compounds of the invention can be formulated as solutions, emulsions, suspensions, powders, foams, pastes, granules, aerosols, microencapsulations in polymeric substances and in coating materials for seed, and also as ULV cold and warm fogging formulations.

The active compounds can be used neat, or in the form of a formulation, e.g. ready-to-use solutions, emulsions, water- or oil-based suspensions, powders, wettable powders, pastes, soluble powders, dusts, soluble granules, granules for broadcasting, suspoemulsion concentrates, natural substances impregnated with active compound, synthetic substances impregnated with active compound, fertilizers and also microencapsulations in polymeric substances. Application may be carried out, for example, by watering, spraying, atomizing, broadcasting, dusting, foaming, spreading, etc. It is also possible to apply the active compounds by the ultra-low volume method or to inject the preparation of active compound or the active compound itself into the soil. It is also possible to treat the seed of the plants.

Formulations containing the compounds of the invention are produced in a known manner, for example by mixing the compounds with extenders (e.g. liquid solvents and/or solid carriers), optionally with the use of surfactants (e.g. emulsifiers and/or dispersants and/or foam-formers). The formulations are prepared either in factories/production plants or alternatively before or during the application.

Auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulfones and sulfoxides (such as dimethyl sulfoxide).

If the extender used is water, it is also possible to use, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and also their ethers and esters, ketones such as acetone, methyl ethyl ketone, methyl isobutyl ketone or cyclohexanone, strongly polar solvents such as dimethylformamide and dimethyl sulfoxide.

Suitable solid carriers are: for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and also protein hydrolysates; suitable dispersants are nonionic and/or ionic substances, for example from the classes of the alcohol-POE and/or -POP ethers, acid and/or POP-POE esters, alkylaryl and/or POP-POE ethers, fat- and/or POP-POE adducts, POE- and/or POP-polyol derivatives, POE- and/or POP-sorbitan- or -sugar adducts, alkyl or aryl sulfates, alkyl- or arylsulfonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulfonic acid derivatives, unmodified and modified celluloses, aromatic and/or aliphatic sulfonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

Further additives may be mineral and vegetable oils. It is also possible to add colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc. Other possible additives are perfumes, mineral or vegetable, optionally modified oils and waxes.

The formulations may also comprise stabilizers, e.g. low-temperature stabilizers, preservatives, antioxidants, light stabilizers or other agents which improve chemical and/or physical stability.

The formulations generally comprise between 0.01 and 98% by weight of active compound, preferably between 0.1 and 95% and particularly preferably between 0.5 and 90%.

The active compounds of the invention can also be used as a mixture with other known fungicides, for example, to improve the activity spectrum or to reduce or slow the development of resistance. A mixture with other known active compounds such as nematicides, herbicides, insecticides, acaricides, or bactericides, or with fertilizers and growth regulators, safeners or semiochemicals is also possible.

Exemplary application rates of the active compounds according to the invention are: when treating leaves: from 0.1 to 10 000 g/ha, preferably from 10 to 1000 g/ha, particularly preferably from 50 to 300 g/ha (when the application is carried out by watering or dripping, it is even possible to reduce the application rate, especially when inert substrates such as rock wool or perlite are used); when treating seed: from 2 to 200 g per 100 kg of seed, preferably from 2.5 to 150 g per 100 kg of seed, and particularly preferably from 2.5 to 25 g per 100 kg of seed, very particularly preferably from 2.5 to 12.5 g per 100 kg of seed; when treating the soil: from 0.1 to 10000 g/ha, preferably from 1 to 5000 g/ha.

The compositions according to the invention are suitable for protecting any plant variety which is employed in agriculture, in the greenhouse, in forests or in horticulture and, in particular, cereals (e.g. wheat, barley, rye, millet and oats), maize, cotton, soya beans, rice, potatoes, sunflowers, beans, coffee, beet (for example sugar beet and fodder beet), peanuts, vegetables (e.g. tomatoes, cucumbers, onions and lettuce), lawns, fruit and nut trees (e.g. apples pears peaches nectarines, apricots, hazelnut, pecan, macadamia, pistachio), soft fruit (e.g. strawberries, raspberries, blackcurrants, redcurrants), grapevines, bananas, cocoa and ornamental plants.

The active compounds of the invention, in combination with good plant tolerance and favourable toxicity to warm-blooded animals and being tolerated well by the environment, are suitable for protecting plants and plant organs, for increasing the harvest yields, for improving the quality of the harvested material and for controlling pests, in particular fungal diseases, which are encountered in agriculture, in horticulture, in animal husbandry, in forests, in gardens and leisure facilities, in the protection of stored products and of materials, and in the hygiene sector. They may be preferably employed as crop protection agents.

Use as Fungicides

The compounds of the invention have activity as fungicides.

The following are illustrative examples of agricultural pests that may be controlled by fungicidal compounds:

Powdery mildew diseases such as: Blumeria diseases, caused for example by Blumeria graminis; Podosphaera diseases, caused for example by Podosphaera leucotheca; Sphaerotheca diseases, caused for example by Sphaerotheca fuliginea; Uncinula diseases, caused for example by Uncinula necator;

Rust diseases such as: Gymnosporangium diseases, caused for example by Gymnosporangium sabinae; Hemileia diseases, caused for example by Hemileia vastatix; Phakopsora diseases, caused for example by Phakopsora pachyrhizi or Phakopsora meibomiae; Puccinia diseases, caused for example by Puccinia recondita; Uromyces diseases, caused for example by Uromyces appendiculatus;

Oomycete diseases such as: Albugo diseases caused for example by Albugo Candida; Bremia diseases, caused for example by Bremia lactucae; Peronospora diseases, caused for example by Peronospora pisi or P. brassicae; Phytophthora diseases, caused for example by Phytophthora infestans; Plasmopara diseases, caused for example by Plasmopara viticola; Pseudoperonospora diseases, caused for example by Pseudoperonospora humuli or Pseudoperonospora cubensis; Pythium diseases, caused for example by Pythium ultimum;

Leafspot, leaf blotch and leaf blight diseases such as: *Alternaria* diseases, caused for example by *Alternaria solani;* Cercospora diseases, caused for example by Cercospora beticola; Cladosporium diseases, caused for example by Cladosporium cucumerinum; Cochliobolus diseases, caused for example by Cochliobolus sativus; Colletotrichum diseases, caused for example by Colletotrichum lindemuthanium; Cycloconium diseases, caused for example by Cycloconium oleaginum; Diaporthe diseases, caused for example by Diaporthe citri;

Drechslera, Syn: Helminthosporium) or Cochliobolus miyabeanus; Elsinoe diseases, caused for example by Elsinoe fawcettii; Gloeosporium diseases, caused for example by Gloeosporium laeticolor; Glomerella diseases, caused for example by Glomerella cingulata; Guignardia diseases, caused for example by Guignardia bidwelli; Leptosphaeria diseases, caused for example by Leptosphaeria maculans; Leptosphaeria nodorum; Magnaporthe diseases, caused for example by Magnaporthe grisea; Mycosphaerella diseases, caused for example by Mycosphaerella graminicola; Mycosphaerella arachidtola; Mycosphaerella fibensis; Phaeosphaeria diseases, caused for example by Phaeosphaera nodorum; Pyrenophora diseases, caused for example by Pyrenophora teres; Ramularia diseases, caused for example by Ramularia collo-cygni; Rhynchosporium diseases, caused for example by Rhynchosporium secalis; Septoria diseases, caused for example by Septoria apii or Septoria lycopercisi; Typhula diseases, caused for example by Typhula incarnata; Venturia diseases, caused for example by Venturia inaequalis;

Root and stem diseases such as: Corticium diseases, caused for example by Corticium graminearum; Fusarium diseases, caused for example by Fusarium oxysporum; Gaeumannomyces diseases, caused for example by Gaeumannomyces graminis; *Rhizoctonia* diseases, caused for example by *Rhizoctonia solani;* Sarocladium diseases caused for example by Sarocladium oryzae; Sclerotium diseases caused for example by Sclerotium oryzae; Tapesia diseases, caused for example by Tapesia acuformis; Thielavbpsis diseases, caused for example by Thielaviopsis basicola;

Ear and panicle diseases including maize cob, such as: *Alternaria* diseases, caused for example by *Alternaria* spp.; Aspergillus diseases, caused for example by Aspergillus flavus; Cladosporium diseases, caused for example by Cladosporium spp.; Claviceps diseases, caused for example by Claviceps purpurea; Fusarium diseases, caused for example by Fusarium culmorum; Gibberella diseases, caused for example by Gibberella zeae; Monographella diseases, caused for example by Monographella nivalis;

Smut and bunt diseases such as: Sphacelotheca diseases, caused for example by Sphacelotheca reiliana; Tilletia diseases, caused for example by Tilletia caries; Urocystis diseases, caused for example by Urocystis occulta; Ustilago diseases, caused for example by Ustilago nuda;

Fruit rot and mould diseases such as: Aspergillus diseases, caused for example by Aspergillus flavus; *Botrytis* diseases, caused for example by *Botrytis cinerea;* Penicillium diseases, caused for example by Penicillium expansum; Rhizopus diseases caused by example by Rhizopus stolonifer; Sclerotinia diseases, caused for example by Sclerotinia sclerotiorum;

Verticilium diseases, caused for example by Verticilium alboatrum;

Seed and soil borne decay, mould, wilt, rot and dampingoff diseases such as: *Alternaria* diseases, caused for example by *Alternaria brassicicola;* Aphanomyces diseases, caused for example by Aphanomyces euteiches; Ascochyta diseases, caused for example by Ascochyta lentis Aspergillus diseases, caused for example by Aspergillus flavus; Cladosporium diseases, caused for example by Cladosporium herbarum; Cochliobolus diseases, caused for example by Cochliobolus sativus (Conidiaform: Drechslera, Bipolaris Syn: Helminthosporium); Colletotrichum diseases, caused for example by Colletotrichum coccodes; Fusarium diseases, caused for example by Fusarium culmorum; Gibberella diseases, caused for example by Gibberella zeae; Macrophomina diseases, caused for example by Macrophomina phaseolina Monographella diseases, caused for example by Monographella nivalis; Penicillium diseases, caused for example by Penicillium expansum; Phoma diseases, caused for example by Phoma lingam; Phomopsis diseases, caused for example by Phomopsis sojae; Phytophthora diseases, caused for example by Phytophthora cactorum; Pyrenophora diseases, caused for example by Pyrenophora graminea Pyricularia diseases, caused for example by Pyricularia oryzae; Pythium diseases, caused for example by Pythium ultimum; *Rhizoctonia* diseases, caused for example by *Rhizoctonia solani;* Rhizopus diseases, caused for example by Rhizopus oryzae; Sclerotium diseases, caused for example by Sclerotium rolfsii; Septoria diseases, caused for example by Septoria nodorum; Typhula diseases, caused for example by Typhula incarnata; Verticillium diseases, caused for example by Verticillium dahliae;

Canker, broom and dieback diseases such as: Nectria diseases, caused for example by Nectria galligena;

Blight diseases such as:

Monilinia diseases, caused for example by Monilinia laxa;

Leaf blister or leaf curl diseases such as: Exobasidium diseases caused for example by Exobasidium vexans; Taphrina diseases, caused for example by Taphrina deformans;—

Decline diseases of wooden plants such as:

Esca diseases, caused for example by Phaemoniella clamydospora, Phaeomoniella clamydospora, Phaeoacremonium aleophilum and Fomitiporia mediterranea;

Eutypa dyeback, caused for example by Eutypa lata; Dutch elm disease, caused for example by Ceratocystsc ulmi; Ganoderma diseases caused by example by Ganoderma boninense; Diseases of flowers and seeds such as: *Botrytis* diseases, caused for example by *Botrytis cinerea;*

Diseases of tubers such as: *Rhizoctonia* diseases, caused for example by *Rhizoctonia solani* Helminthosporium diseases, caused for example by Helminthospohum solani.

Diseases of Tubers such as

*Rhizoctonia* diseases caused for example by *Rhizoctonia solani;* Helminthosporium diseases caused for example by Helminthospohum solani;

Club root diseases such as

Plasmodiophora diseases, caused for example by Plamodiophora brassicae.

The compounds of the invention may be active against a broad spectrum of fungal diseases of plants. Alternatively they may be active specifically against cereal fungal diseases or they may be specifically active against oomycete diseases.

Notable cereal fungal pathogens are:

Erisyphe graminis (now Blumeria)

*Septoria nodorum*

*Septoria tritici*

Fusarium oxysporum

Rhychosporium secalis

Pyrenophora teres

It may be that the compounds of the invention are for use in treating a fungal disease caused by a pathogen selected from *Botrytis cinerea,* an *Alternaria* species, *Septoria tritici* and *Rhizoctonia cerealis.*

Notable oomycete fungal pathogens are:

Plasmopara viticola

Phytophthora infestans

Pythium ultimum

Bremia lactuca

Peronospora spp

In additional to their fungicidal activity, the compounds of the invention may also have activity against other microbes, e.g. bacteria.

The fungicidal compounds of the invention may also be used in the treatment of fungal diseases of humans and animals (e.g. mammals). Likewise, the bactericidal compounds of the invention may be used in the treatment of bacterial diseases of humans and animals. Thus, the invention includes a method of treating a fungal or bacterial disease, the method comprising administering a therapeutic amount of an antifungal agent of the invention to a subject (e.g. a human subject) in need thereof. The compound may be formulated for topical administration to the infected area of the body or it may be formulated for oral or parenteral administration.

Detailed Description—Synthesis

The skilled person will appreciate that adaptation of methods known in the art could be applied in the manufacture of the compounds of the present invention.

For example, the skilled person will be immediately familiar with standard textbooks such as "Comprehensive Organic Transformations—A Guide to Functional Group Transformations", R C Larock, Wiley-VCH (1999 or later editions); "March's Advanced Organic Chemistry—Reactions, Mechanisms and Structure", M B Smith, J. March, Wiley, (5th edition or later); "Advanced Organic Chemistry, Part B, Reactions and Synthesis", F A Carey, R J Sundberg, Kluwer Academic/Plenum Publications, (2001 or later editions); "Organic Synthesis—The Disconnection Approach", S Warren (Wiley), (1982 or later editions); "Designing Organic Syntheses" S Warren (Wiley) (1983 or later editions); "Heterocyclic Chemistry", J. Joule (Wiley 2010 edition or later); ("Guidebook To Organic Synthesis" R K Mackie and D M Smith (Longman) (1982 or later editions), etc., and the references therein as a guide.

The skilled person is familiar with a range of strategies for synthesising organic and particularly heterocyclic molecules and these represent common general knowledge as set out in text books such as Warren "Organic Synthesis: The Disconnection Approach"; Mackie and Smith "Guidebook to Organic Chemistry"; and Clayden, Greeves, Warren and Wothers "Organic Chemistry".

The skilled person will exercise his judgement and skill as to the most efficient sequence of reactions for synthesis of a given target compound and will employ protecting groups as necessary. This will depend inter alia on factors such as the nature of other functional groups present in a particular substrate. Clearly, the type of chemistry involved will influence the choice of reagent that is used in the said synthetic steps, the need, and type, of protecting groups that are employed, and the sequence for accomplishing the protection/deprotection steps. These and other reaction parameters will be evident to the skilled person by reference to standard textbooks and to the examples provided herein.

Sensitive functional groups may need to be protected and deprotected during synthesis of a compound of the invention. This may be achieved by conventional methods, for example as described in "Protective Groups in Organic Synthesis" by T W Greene and P G M Wuts, John Wiley & Sons Inc. (1999), and references therein.

Throughout this specification these abbreviations have the following meanings:

| | |
|---|---|
| aq.—aqueous | dba—dibenzylideneacetone |
| DBU—1,8-Diazabicyclo[5.4.0]undec-7-ene | DMF—N,N-dimethylformamide |
| DMSO—dimethylsulfoxide | h—hours |

| | |
|---|---|
| PE petroleum ether | THF—tetrahydrofuran |
| Xantphos—4,5-Bis(diphenylphosphino)-9,9-dimethylxanthene | |
| r.t.—room temperature | |

Certain compounds of the invention can be accessed according to or analogously to the general synthetic schemes below. Certain compounds of the invention can be accessed via the synthetic intermediates described in Examples 1 to 27 below.

General Synthetic Schemes

Certain compounds of the invention can be made according to scheme A. Suzuki reaction between iodide A and boronic acid B (e.g. using Na$_2$CO$_3$, Pd(PPh$_3$)$_4$ in dioxane/water at 90° C.) can provide biaryl C which can be coupled with benzimidazole/benzotriazole D (Pd$_2$dba$_3$, Xantphos, Cs$_2$CO$_3$ in dioxane at 100° C.) to provide compounds of formula E. This can be used to produce compounds in which Y$^1$ is either CH or N.

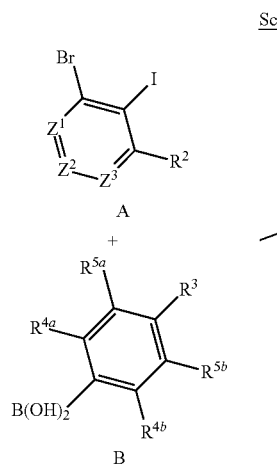

Scheme A

Certain pyridazine compounds of the invention can be made according to scheme B. Benzimidazole/benzotriazole D can be converted to bromide F (e.g. by reaction with bromoacetyl chloride in acetone in the presence of K$_2$CO$_3$ at reflux). Reaction of bromide F with carboxylic acid G in the presence of a base (e.g. Et$_3$N and DBU in the presence of air) can provide butanolide H. Subsequent treatment with hydrazine followed by POCl$_3$ can provide pyridazine J (a subset of compounds of formula I). This can be used to produce compounds in which Y$^1$ is either CH or N.

Scheme B

Certain pyrimidine compounds of the invention can be made according to scheme C. Chloro pyrimidine K can be converted to amino pyrimidine L (e.g. by heating with NH₄OH). Suzuki reaction between amino pyrimidine L and boronic acid B (e.g. using Na₂CO₃, Pd(PPh₃)₄ in dioxane/water at 90° C.) can provide biaryl M which can be coupled with nitrobenzene D (e.g. by deprotonating the amine group on pyrimidine L with NaH and reacting with nitrobenzene N in DMF at room temperature) to provide compounds of formula O. Reduction of the nitro group (e.g. using Fe, NH₄Cl in THF/water/methanol at 60° C.) followed by reaction with methyl orthoformate in the presence of an acid (e.g. HCl) and at high temperature (e.g. 100° C.) can provide pyrimidine P (a subset of compounds of formula I).

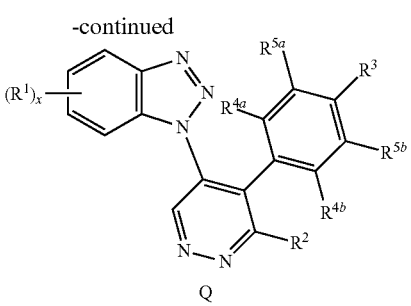

EXAMPLES

General Methods

Flash chromatography was carried out using a Biotage Isolera 4, with Biotage® SNAP KP-Sil cartridges, packed Scheme C

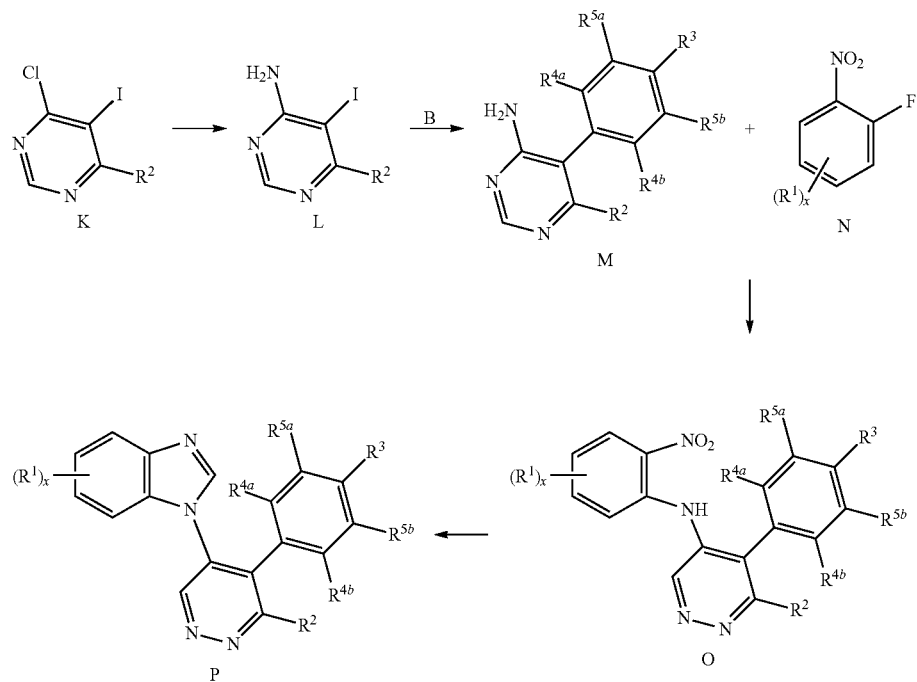

Certain pyrimidine compounds of the invention can be made according to scheme D. Reduction of nitrate O (e.g. using Fe, NH₄Cl in THF, MeOH, H₂O) followed by triazole formation (e.g. using NaNO₂ and HCl) can provide triazole.

Scheme D

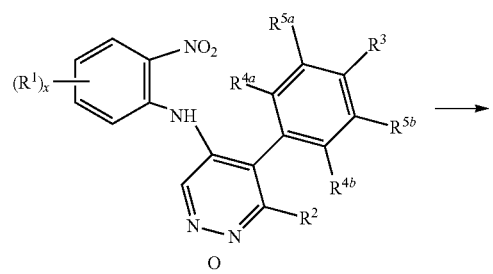

with 50 μm silica particles with a surface area of 500 m²/g, or alternative cartridges (e.g. Puriflash, produced by Interchim) where stated, or using silica gel (40-63 μm particles). Visualisation was carried out with UV light (254 nm) and by staining with either potassium permanganate, phosphomolybdic acid (PMA) or ninhydrin solutions.

All ¹H NMR spectra were obtained on a Bruker AVIII 400 with 5 mm QNP or Bruker AVI 500 with 5 mm QNP. Chemical shifts are expressed in parts per million (δ) and are referenced to the solvent. Coupling constants J are expressed in Hertz (Hz).

MS was carried out on a Waters Alliance ZQ MS, using a YMC-Triart C18 50×2 mm, 5 micron LC column (solvent: 5-90% gradient of acetonitrile in water (with 1% by volume of 28% (by weight) aqueous ammonia solution)) by Method A. Flow rate 0.8 mL/min. Wavelengths were 254 and 210 nM.

Method A (5 Minute Basic pH)

Column: YMC-Triart C18 50×2 mm, 5 µm. Flow rate: 0.8 mL/min. Injection volume: 5 µL.
Mobile Phase A H₂O
B CH₃CN
C 50% H₂O/50% CH₃CN+1.0% ammonia (aq.)

| Time (min) | A (%) | B (%) | C (%) |
|---|---|---|---|
| 0 | 95 | 0 | 5 |
| 4 | 0 | 95 | 5 |
| 4.4 | 0 | 95 | 5 |
| 4.5 | 95 | 5 | 0 |
| 4.5 | | STOP | |

Method E (3.5 Minute Basic pH)

Mobile phases: Water (A)/Acetonitrile (B) both with 0.1% (v/v) Ammonia

| Time | % A | % B | Flow rate (mL/min) |
|---|---|---|---|
| Initial | 98 | 2 | 1.0 |
| 0.2 | 98 | 2 | 1.0 |
| 2.5 | 2 | 98 | 1.0 |
| 3.0 | 2 | 98 | 1.0 |
| 3.1 | 98 | 2 | 1.0 |
| 3.5 | 98 | 2 | 1.0 |

Column: BEH C18 2.1×50mm, 1.7 µm@50° C.

Method F (3.5 Minute Acidic pH)

Mobile phases: Water (A)/Acetonitrile (B) both with 0.1% (v/v) Formic Acid

| Time | % A | % B | Flow rate (mL/min) |
|---|---|---|---|
| Initial | 98 | 2 | 1.0 |
| 0.2 | 98 | 2 | 1.0 |
| 2.5 | 2 | 98 | 1.0 |
| 3.0 | 2 | 98 | 1.0 |
| 3.1 | 98 | 2 | 1.0 |
| 3.5 | 98 | 2 | 1.0 |

Column: CSH C18 2.1×50 mm, 1.7 µm@50° C.

All reagents were obtained from commercial suppliers and used as supplied unless otherwise stated.

All compounds are named using ChemBioDraw Ultra 14.0.

Intermediate A: 5-Iodo-6-methylpyrimidin-4-amine

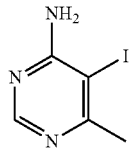

A suspension of 4-chloro-5-iodo-6-methylpyrimidine (170 mg, 0.668 mmol) in ammonium hydroxide (28%, 2 mL) was heated to 100° C. in a sealed tube for 3 h. After cooling to room temperature, the suspension was filtered, and the solid washed (water) and dried under vacuum to yield the title compound as a pale orange solid (90 mg, 57%). ¹H NMR $\delta_H$ (500 MHz, CDCl₃) 8.33 (s, 1H), 5.46 (br s, 2H), 2.64 (s, 3H). LCMS (Method A): 1.66 min (236.0, MH⁺).

Intermediate B: 5-(2-Chloro-4-fluorophenyl)-6-methylpyrimidin-4-amine

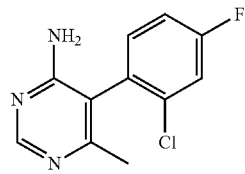 [SMILES: Cc1ncnc(N)c1-c1ccc(F)cc1Cl]

Intermediate A (90 mg, 0.38 mmol) and 2-chloro-4-fluorophenylboronic acid (100 mg, 0.57 mmol) were dissolved in 1,4-dioxane (3 mL). Sodium carbonate (2 M aq) (0.78 mL, 1.5 mmol) was added and the mixture degassed by nitrogen bubbling for 5 min.

Tetrakis(triphenylphosphine)palladium (22 mg, 20 µmol) was added, and the reaction was heated to 90° C. for 16 h. The reaction was filtered through decalite®, eluting with EtOAc, and concentrated in vacuo. The residue was purified by chromatography (SiO₂, 0-100% EtOAc in PE) and the title compound was isolated as an orange solid (82 mg, 90%). ¹H NMR $\delta_H$ (500 MHz, CDCl₃) 8.53 (s, 1H), 7.34 (dd, J=8.4, 2.6 Hz, 1H), 7.29-7.24 (m, 1H), 7.15 (td, J=8.2, 2.6 Hz, 1H), 4.62 (br s, 2H), 2.13 (s, 3H). LCMS (Method A): 2.22 min (238.1, MH⁺).

Intermediates C-G

The following Intermediates were prepared using the general method described for Intermediate B from the appropriate halo (hetero)-aromatic and boronic acid.

| Intermediate No. | Compound | ¹H NMR/LCMS |
|---|---|---|
| C | 5-(2-Chloro-4-methoxyphenyl)-6-methylpyrimidin-4-amine | (500 MHz, CDCl₃) δ 8.51 (s, 1H), 7.16 (d, J = 8.5 Hz, 1H), 7.11 (d, J = 2.6 Hz, 1H), 6.95 (dd, J = 8.5, 2.6 Hz, 1H), 4.62 (br s, 2H), 3.87 (s, 3H), 2.14 (s, 3H). LCMS (Method A): 2.27 min (250.3, MH⁺) |

| Intermediate No. | Compound | $^1$H NMR/LCMS |
|---|---|---|
| D | 5-(2-Chlorophenyl)-6-methylpyrimidin-4-amine | (500 MHz, CDCl$_3$) δ 8.53 (s, 1H), 7.60-7.52 (m, 1H), 7.44-7.39 (m, 2H), 7.28-7.26 (m, 1H), 4.60 (br s, 2H), 2.14 (s, 3H). LCMS (Method A): 2.13 min (220.3, MH$^+$). |
| E | 3-(2-Chloro-4-fluorophenyl)-4-methylpyridin-2-amine | (500 MHz, CDCl$_3$) δ 8.00 (d, J = 5.2 Hz, 1H), 7.31 (dd, J = 8.5, 2.6 Hz, 1H), 7.24 (dd, J = 8.5, 6.1 Hz, 1H), 7.12 (td, J = 8.2, 2.6 Hz, 1H), 6.64 (d, J = 5.2 Hz, 1H), 4.13 (br s, 2H), 1.96 (s, 3H). LCMS (Method A): 2.85 min (237.2, MH$^+$). |
| F | 2-Chloro-3-(2-chloro-4-fluorophenyl)pyridin-4-amine | (500 MHz, CDCl$_3$) δ 8.03 (d, J = 5.6 Hz, 1H), 7.32 (dd, J = 8.4, 2.5 Hz, 1H), 7.28 (dd, J = 8.3, 5.8 Hz, 1H), 7.14 (td, J = 8.3, 2.6 Hz, 1H), 6.59 (d, J = 5.6 Hz, 1H), 4.12 (br s, 2H). LCMS (Method E): 2.73 min (258.9, MH$^+$). |
| G | 2'-Chloro-4'-fluoro-6-methyl-[1,1'-biphenyl]-2-amine | (500 MHz, CDCl3) δ 7.33 (dd, J = 8.6, 2.6 Hz, 1H), 7.27 (dd, J = 8.5, 6.2 Hz, 1H), 7.19-7.08 (m, 2H), 6.77 (d, J = 7.5 Hz, 1H), 6.71 (d, J = 8.0 Hz, 1H), 3.80 (br s, 2H), 1.99 (s, 3H). LCMS (Method A): 3.80 min (236.1, MH$^+$). |

Intermediate H: 5-(2-Chloro-4-fluorophenyl)-N-(2,4-difluoro-6-nitrophenyl)-6-methylpyrimidin-4-amine

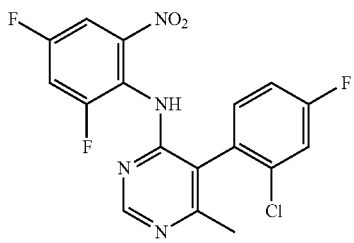 [SMILES: Cc1ncnc(Nc2c(F)cc(F)cc2[N+](=O)[O-])c1-c1ccc(F)cc1Cl]

Sodium hydride (60%, 55 mg, 1.4 mmol) was added to a solution of Intermediate B in DMF (2 mL). After stirring at room temperature for 15 min, 1,2,5-trifluoro-3-nitrobenzene (63 μL, 0.56 mmol) was added, and stirring continued for 90 min. The reaction mixture was quenched cautiously with water, and extracted with EtOAc (×3). The combined organic phases were washed with brine, dried (MgSO$_4$) and concentrated in vacuo. The residue was purified by chromatography (SiO$_2$, 0-50% EtOAc in PE) and the title compound was isolated as a yellow solid (129 mg, 70%). $^1$H NMR δ$_H$ (500 MHz, CDCl$_3$) 8.61 (s, 1H), 7.66-7.61 (m, 1H), 7.41 (dd, J=8.3, 2.5 Hz, 1H), 7.37 (dd, J=8.5, 5.9 Hz, 1H), 7.25-7.21 (m, 2H), 7.13 (br s, 1H), 2.23 (s, 3H).
LCMS (Method A): 3.17 min (395.3, MH$^+$).

Intermediates I-L

The following Intermediates were prepared using the general method described for Intermediate H from the appropriate Intermediate (C-F) and 1,2,5-trifluoro-3-nitrobenzene.

| Intermediate No. | Compound | ¹H NMR/LCMS |
|---|---|---|
| I | 5-(2-Chloro-4-methoxyphenyl)-N-(2,4-difluoro-6-nitrophenyl)-6-methylpyrimidin-4-amine | (500 MHz, CDCl₃) δ 8.58 (s, 1H), 7.67-7.56 (m, 1H), 7.26-7.16 (m, 4H), 7.07-7.01 (m, 1H), 3.89 (s, 3H), 2.23 (s, 3H). LCMS (Method A): 3.20 min (407.3, MH⁺). |
| J | 5-(2-Chlorophenyl)-N-(2,4-difluoro-6-nitrophenyl)-6-methylpyrimidin-4-amine | (500 MHz, CDCl₃) δ 8.61 (s, 1H), 7.68-7.59 (m, 2H), 7.53-7.47 (m, 2H), 7.39-7.36 (m, 1H), 7.22 (ddd, J = 9.7, 7.7, 2.9 Hz, 1H), 7.16 (br s, 1H), 2.23 (s, 3H). LCMS (Method A): 3.14 min (377.3, MH⁺). |
| K | 3-(2-Chloro-4-fluorophenyl)-N-(2,4-difluoro-6-nitrophenyl)-4-methylpyridin-2-amine | (500 MHz, CDCl₃) δ 8.07 (d, J = 5.1 Hz, 1H), 7.64-7.58 (m, 1H), 7.42-7.35 (m, 2H), 7.33 (dd, J = 8.5, 6.0 Hz, 1H), 7.24-7.12 (m, 2H), 6.87 (d, J = 5.2 Hz, 1H), 2.05 (s, 3H). LCMS (Method A): 3.72 min (394.3, MH⁺). |
| L | 2-Chloro-3-(2-chloro-4-fluorophenyl)-N-(2,4-difluoro-6-nitrophenyl)pyridin-4-amine | (500 MHz, CDCl₃) δ 8.20 (d, J = 5.7 Hz, 1H), 7.72-7.64 (m, 1H), 7.43-7.35 (m, 2H), 7.33-7.27 (m, 1H), 7.25-7.19 (m, 2H), 6.50 (t, J = 6.0 Hz, 1H). LCMS (Method A): 3.43 min (414.2, MH⁺). |

Intermediate M: 2'-Chloro-N-(2,4-difluoro-6-nitrophenyl)-4'-fluoro-6-methyl-[1,1'-biphenyl]-2-amine

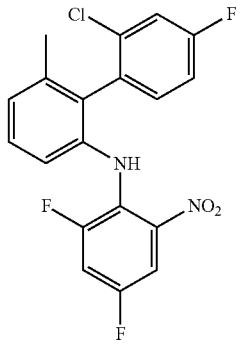 [SMILES: Cc1cccc(Nc2c(F)cc(F)cc2[N+](=O)[O-])c1-c1ccc(F)cc1Cl]

Intermediate G (90 mg, 0.38 mmol), 2-bromo-1,5-difluoro-3-nitrobenzene (57 µL, 0.46 mmol), caesium carbonate (174 mg, 0.535 mmol) and 4,5-bis(diphenylphosphino)-9,9-dimethylxanthene (44 mg, 0.08 mmol) were dissolved in 1,4-dioxane (1 mL). The mixture was degassed by nitrogen bubbling for 5 min. Tris(dibenzylideneacetone)dipalladium (0) (70 mg, 0.08 mmol) was added, and the reaction was heated to 100° C. for 16 h. After cooling to room temperature the mixture was partitioned between EtOAc and water. The aqueous layer was extracted with EtOAc. The combined organic layers were washed (brine), dried (MgSO$_4$) and concentrated in vacuo. The residue was purified by chromatography (SiO$_2$, 0-100% EtOAc in PE) and the title compound was isolated as a red oil (111 mg, 74%). $^1$H NMR $\delta_H$ (500 MHz, CDCl$_3$) 7.87 (br s, 1H), 7.66 (ddd, J=8.5, 3.0, 2.0 Hz, 1H), 7.49 (ddd, J=7.5, 2.8, 2.0 Hz, 1H), 7.32 (dd, J=8.5, 2.6 Hz, 1H), 7.27-7.22 (m, 1H), 7.20 (td, J=7.8, 2.9 Hz, 1H), 7.17-7.10 (m, 1H), 7.10-7.05 (m, 1H), 6.78 (dd, J=8.0, 5.2 Hz, 1H), 2.07 (s, 3H).

Intermediate N: N$^1$-(5-(2-Chloro-4-fluorophenyl)-6-methylpyrimidin-4-yl)-4,6-difluorobenzene-1,2-diamine

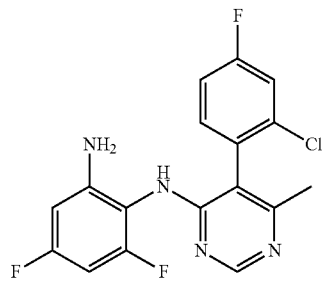 [SMILES: Cc1ncnc(Nc2c(N)cc(F)cc2F)c1-c1ccc(F)cc1Cl]

A solution of ammonium chloride (51 mg, 0.95 mmol) in water (0.4 mL) was added to a solution of Intermediate H (125 mg, 0.317 mmol) in THF (2 mL)/methanol (1 mL). Iron powder (53 mg, 0.95 mmol) was added, and the mixture was heated to 65° C. for 18 h. After cooling to room temperature, the mixture was filtered through decalite®, eluting with EtOAc. The filtrate was washed (water, brine), dried (MgSO$_4$) and concentrated in vacuo to yield the title compound as an off-white solid (116 mg, quant.). $^1$H NMR $\delta_H$ (500 MHz, CDCl$_3$) 8.61 (s, 1H), 7.44-7.33 (m, 2H), 7.24-7.17 (m, 1H), 6.35-6.20 (m, 2H), 5.29 (s, 1H), 4.13 (br s, 2H), 2.18 (s, 3H). LCMS (Method A): 2.84 min (365.3, MH$^+$).

Intermediates O-S

The following Intermediates were prepared using the general method described for Intermediate N from the appropriate Intermediate (I-M).

| Intermediate No. | Compound | $^1$H NMR/LCMS |
|---|---|---|
| O | N$^1$-(5-(2-Chloro-4-methoxyphenyl)-6-methylpyrimidin-4-yl)-4,6-difluorobenzene-1,2-diamine | (500 MHz, CDCl$_3$) δ 8.59 (s, 1H), 7.29-7.26 (m, 1H), 7.15 (d, J = 2.5 Hz, 1H), 7.00 (dd, J = 8.5, 2.6 Hz, 1H), 6.31-6.22 (m, 2H), 5.37 (br s, 1H), 4.14 (br s, 2H), 3.88 (s, 3H), 2.19 (s, 3H). LCMS (Method A): 2.87 min (377.2, MH$^+$). |

| Intermediate No. | Compound | ¹H NMR/LCMS |
|---|---|---|
| P | N¹-(5-(2-Chlorophenyl)-6-methylpyrimidin-4-yl)-4,6-difluorobenzene-1,2-diamine | (500 MHz, CDCl₃) δ 8.61 (s, 1H), 7.65-7.58 (m, 1H), 7.51-7.42 (m, 2H), 7.42-7.35 (m, 1H), 6.33-6.21 (m, 2H), 5.30 (br s, 1H), 4.13 (br s, 2H), 2.19 (s, 3H). LCMS (Method A): 2.81 min (347.2, MH⁺). |
| Q | N¹-(3-(2-Chloro-4-fluorophenyl)-4-methylpyridin-2-yl)-4,6-difluorobenzene-1,2-diamine | (500 MHz, CDCl₃) δ 8.07 (d, J = 5.2 Hz, 1H), 7.40-7.30 (m, 2H), 7.22-7.12 (m, 1H), 6.70 (d, J = 5.2 Hz, 1H), 6.31-6.18 (m, 2H), 4.99 (br s, 1H), 4.23 (br s, 2H), 1.99 (s, 3H). LCMS (Method A): 3.35 min (364.3, MH⁺). |
| R | N¹-(2-Chloro-3-(2-chloro-4-fluorophenyl)pyridin-4-yl)-4,6-difluorobenzene-1,2-diamine | (500 MHz, CDCl₃) δ 8.07 (d, J = 5.7 Hz, 1H), 7.41 (dd, J = 8.5, 6.0 Hz, 1H), 7.37 (dd, J = 8.4, 2.5 Hz, 1H), 7.21 (td, J = 8.2, 2.6 Hz, 1H), 6.34-6.23 (m, 3H), 4.88 (br s, 1H), 4.12 (br s, 2H). LCMS (Method A): 3.33 min (386.0, MH⁺). |
| S | N¹-(2'-Chloro-4'-fluoro-6-methyl-[1,1'-biphenyl]-2-yl)-4,6-difluorobenzene-1,2-diamine | LCMS (Method A): 4.32 min (363.0, MH⁺). |

Intermediate T: 3-Methyl-2-(4,4,5,5-tetramethyl-1,3,2-dioxaborolan-2-yl)aniline

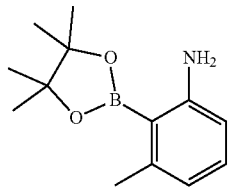 [SMILES: Cc1cccc(N)c1B1OC(C)(C)C(C)(C)O1]

To a solution of 2-bromo-3-methylaniline (0.34 mL, 2.7 mmol) in 1,4-dioxane (12 mL) was added potassium acetate (527 mg, 5.37 mmol), bis(pinacolato)diboron (1365 mg, 5.37 mmol) and the solution was degassed for 10 min. [1,1'-Bis(diphenylphosphino)ferrocene]dichloropalladium (II), complex with dichloromethane (219 mg, 0.269 mmol) were added and the suspension was heated to 90° C. for 18 h in a closed vessel. The reaction mixture was allowed to cool, diluted with EtOAc then washed with brine. The organic layer was dried over MgSO$_4$, and concentrated in vacuo. The residue was purified by chromatography (SiO$_2$, 0-20% EtOAc in PE) and the title compound was isolated as a white solid (742 mg, 65%). $^1$H NMR $\delta_H$ (500 MHz, CDCl$_3$) 7.04 (t, J=7.7 Hz, 1H), 6.49 (m, 2H), 4.20 (s, 2H), 2.44 (s, 3H), 1.34 (s, 12H). LCMS (Method A): 4.15 min (234.2, MH+).

Intermediate U: 2'-Chloro-4'-fluoro-6-methyl-N-(2-nitrophenyl)-[1,1'-biphenyl]-2-amine

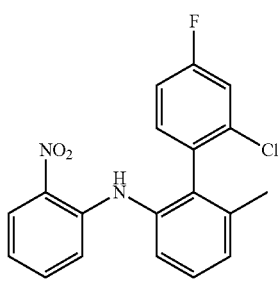 [SMILES: Cc1cccc(Nc2ccccc2[N+](=O)[O-])c1-c1ccc(F)cc1Cl]

Intermediate G (50 mg, 0.21 mmol), 4,5-bis(diphenylphosphino)-9,9-dimethylxanthene (24.55 mg, 0.042 mmol), caesium carbonate (97 mg, 0.297 mmol) and 1-bromo-2-nitrobenzene (47.1 mg, 0.233 mmol) were dissolved in 1,4-dioxane (8 mL). The solution was purged with N$_2$ for 5 min and tris(dibenzylideneacetone)dipalladium(0) (38.9 mg, 0.042 mmol) was added. The solution was heated to 100° C. for 18 h. The reaction mixture was allowed to cool, water was added and the product was extracted with EtOAc. The combined organic layers were washed with brine, dried (MgSO$_4$) and concentrated in vacuo. The residue was purified by chromatography (SiO$_2$, 0-20% EtOAc in PE) and the title compound was isolated as an orange solid (67 mg, 71%). $^1$H NMR $\delta_H$ (500 MHz, CDCl$_3$) 9.00 (s, 1H), 8.08 (dd, J=8.6, 1.5 Hz, 1H), 7.38-7.30 (m, 3H), 7.23 (dt, J=8.7, 2.1 Hz, 2H), 7.20-7.17 (m, 1H), 7.16 (dd, J=8.5, 6.1 Hz, 1H), 7.06-7.02 (m, 1H), 6.71 (ddd, J=8.4, 6.9, 1.3 Hz, 1H), 2.09 (s, 3H). LCMS (Method A): 4.49 min (357.0, MH$^+$).

Intermediate V: 1-Fluoro-2-nitro-4-(prop-2-yn-1-yloxy)benzene

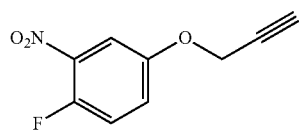

Propargyl bromide (80% in PhMe, 0.355 mL, 3.18 mmol) was added to a solution of 4-fluoro-3-nitrophenol (0.500 g, 3.2 mmol) and potassium carbonate (0.440 g, 3.18 mmol) in DMF (10 mL) at r.t. and the reaction mixture stirred for 3 days. The reaction mixture was then diluted with water and extracted into EtOAc before being dried (MgSO$_4$) and concentrated in vacuo. The residue was purified by chromatography (SiO$_2$, 0-20% EtOAc in PE) and the title compound was isolated as a brown oil (0.620 g, 100%). $^1$H NMR $\delta_H$ (500 MHz, CDCl$_3$) δ 7.67 (dd, J=5.0, 2.1 Hz, 1H), 7.26 (dd, J=5.2, 2.4 Hz, 2H), 4.77 (d, J=2.4 Hz, 2H), 2.60 (t, J=2.4 Hz, 1H).

Intermediate W

The following Intermediate was prepared using the general method described for Intermediate B from 2-bromo-1,3-difluoro-5-methoxybenzene and Intermediate T.

| Intermediate No. | Compound | $^1$H NMR/LCMS |
|---|---|---|
| W | 2',6'–Difluoro-4'-methoxy-6-methyl-[1,1'-biphenyl]-2-amine 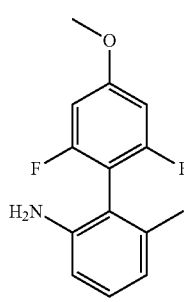 | (500 MHz, CDCl$_3$) δ 7.11 (t, J = 7.8 Hz, 1H), 6.72 (d, J = 7.5 Hz, 1H), 6.65 (d, J = 8.0 Hz, 1H), 6.59 (m, 2H), 3.84 (s, 3H), 3.49 (s, 2H), 2.04 (s, 3H). LCMS (Method A): 3.82 min (250.2, MH$^+$) |

Intermediates X-Y

The following Intermediates were prepared using the general method described for Intermediate B from the appropriate halo (hetero)-aromatic and boronic acid.

| Intermediate No. | Compound | 1H NMR/LCMS |
|---|---|---|
| X | 2-Chloro-3-(2-chloro-4-methoxyphenyl)pyridin-4-amine | (500 MHz, CDCl$_3$) δ 7.95 (d, J = 5.6 Hz, 1H), 7.17 (d, J = 8.5 Hz, 1H), 7.08 (d, J = 2.6 Hz, 1H), 6.93 (dd, J = 8.5, 2.6 Hz, 1H), 6.57 (d, J = 5.6 Hz, 1H), 4.35 (s, 2H), 3.84 (s, 3H). LCMS (Method A): 3.28 min (269.1, MH$^+$). |
| Y | 3-(2-Chloro-4-methoxyphenyl)-4-methylpyridin-2-amine | (500 MHz, CDCl$_3$) δ 7.91 (d, J = 5.6 Hz, 1H), 7.14 (dd, J = 12.9, 5.5 Hz, 2H), 6.97 (dd, J = 8.5, 2.6 Hz, 1H), 6.69 (d, J = 5.7 Hz, 1H), 4.90 (s, 2H), 3.89 (s, 3H), 2.03 (s, 3H). LCMS (Method A): 2.79 min (249.1, MH$^+$). |

Intermediate Z: 2-(2,6-Difluoro-4-methoxyphenyl)-3-oxobutanenitrile

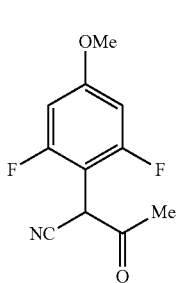

Sodium hydride (177 mg, 4.42 mmol) and anhydrous THF (5.9 mL) were added to a 20 mL microwave vial which was then capped and purged with nitrogen. 2-Chloro-4-fluorophenylacetonitrile (500 mg, 2.95 mmol) was then added dropwise as a solution in THF (1 mL) and the reaction was stirred at r.t. for 5 minutes. EtOAc (2.88 mL, 29.5 mmol) was then added and the reaction was heated to 65° C. for 1 hour. Water (25 mL) and EtOAc (25 mL) were added to the reaction mixture and the layers separated. The aqueous layer was acidified to pH 6 using 1 M aq. HCl and extracted with EtOAc (3×10 mL). The combined organic layers were dried using MgSO$_4$ and concentrated under reduced pressure to afford the title compound as a yellow solid (614 mg, 98%). LCMS (Method F): 1.63 min (210.0, MH$^-$).

Intermediate AA: 5-(2,6-Difluoro-4-methoxyphenyl)-6-methylpyrimidin-4-amine (Trimethylsilyl)diazomethane (0.89 mL, 1.8 mmol) was slowly added to a solution of Intermediate Z (200 mg, 0.888 mmol) in anhydrous DCM (1.8 mL) and stirred for 18 hours at r.t. Acetic acid was added dropwise until gas evolution ceased, indicating the quenching of the remaining (trimethylsilyl)diazomethane. The solution was then concentrated in vacuo to afford a crude oil. The residue was then dissolved in ethanol (5.00 ml) and added to a pre-formed solution of formimidamide hydrochloride (79.0 mg, 0.98 mmol) in 30% sodium ethoxide in EtOH (829 µl, 2.22 mmol). The reaction was then heated at 80° C. for 17 hours. The reaction mixture was allowed to cool to r.t. and the solution was neutralised using acetic acid and concentrated in vacuo to afford a crude black solid. The crude residue was purified using chromatography (SiO$_2$, 50-100% EtOAc in PE). This afforded the title compound as a yellow solid (27.5 mg, 12% yield). $^1$H NMR δ$_H$ (500 MHz, DMSO-d$^6$) δ 8.27 (s, 1H), 6.88 (d, J=9.6 Hz, 2H), 6.53 (br. s, 2H), 3.96-3.61 (s, 3H), 2.06-1.83 (s, 3H).

Intermediate AB

The following Intermediate was prepared using the general method described for Intermediate H from the appropriate Intermediate (W), 1,2,5-trifluoro-3-nitrobenzene and potassium tert-butoxide (2 equivalents) instead of NaH as a base.

Intermediates AC-AD

The following Intermediates were prepared using the general method described for Intermediate U from the appropriate Intermediate and appropriate substituted bromonitrobenzene

| Intermediate No. | Compound | $^1$H NMR/LCMS |
|---|---|---|
| AC | 2'-Chloro-N-(4-chloro-2-nitrophenyl)-4'-fluoro-6-methyl-[1,1'-biphenyl]-2-amine | (500 MHz, CDCl$_3$) δ 8.97 (s, 1H), 8.07 (d, J = 2.5 Hz, 1H), 7.37 (t, J = 7.8 Hz, 1H), 7.28 (dd, J = 2.5, 0.5 Hz, 1H), 7.26-7.21 (m, 3H), 7.16-7.12 (m, 2H), 7.07-7.02 (m, 1H), 2.09 (s, 3H). |
| AD | 2'-Chloro-4'-fluoro-6-methyl-N-(4-methyl-2-nitrophenyl)[1,1'-biphenyl]-2-amine | LCMS (Method A): 4.19 min (371.0, MH$^+$). |

| Intermediate No. | Compound | $^1$H NMR/LCMS |
|---|---|---|
| AB | N-(2,4-Difluoro-6-nitrophenyl)-2',6'-difluoro-4'-methoxy-6-methyl-[1,1'-biphenyl]-2-amine | LCMS (Method A): 4.38 min (407.2, MH$^+$). |

Intermediate AE: N-(4-Chloro-2-fluoro-6-nitrophenyl)-5-(2,6-difluoro-4-methoxyphenyl)-6-methylpyrimidin-4-amine Intermediate AA (176 mg, 0.701 mmol) was dissolved in anhydrous THF (3.5 mL) and the flask was sealed and purged with nitrogen. 2M Sodium bis(trimethylsilyl)amide solution in THF (525 µl, 1.05 mmol) was then added in a dropwise manner and the reaction was allowed to stir for 15 minutes at r.t. 5-Chloro-1,2-difluoro-3-nitrobenzene (136 mg, 0.701 mmol) was then added as a solution in anhydrous THF (0.5 mL) and the reaction was allowed to proceed for approx. 16 hours. The reaction mixture was diluted with water (10 mL), neutralised using 1M aq. HCl and extracted with EtOAc (3×10 mL). The combined organic phases were dried over MgSO$_4$ and concentrated in vacuo to afford a crude solid which was purified using chromatography (SiO$_2$, 0-100% EtOAc in PE) to yield the title compound as a yellow oil (80 mg, 27% yield). $^1$H NMR δ$_H$ (500 MHz, DMSO-d$^6$) δ 8.49 (s, 1H), 8.40 (s, 1H), 8.03-7.95 (m, 2H), 6.97 (d, J=9.8 Hz, 2H), 3.86 (s, 3H), 2.10 (d, J=17.0 Hz, 3H).

Intermediates AF-AN

The following Intermediates were prepared using the general method described for Intermediate AE from the appropriate Intermediate and substituted fluoro-nitrobenzene.

| Intermediate No. | Compound | $^1$H NMR/LCMS |
|---|---|---|
| AF | N-(4-Chloro-2-fluoro-6-nitrophenyl)-5-(2-chloro-4-methoxyphenyl)-6-methylpyrimidin-4-amine 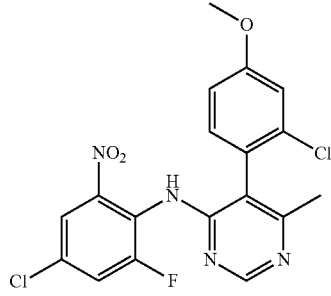 | LCMS (Method A): 3.72 min (423.1, MH$^+$). |
| AG | N-(4-Chloro-2-fluoro-6-nitrophenyl)-5-(2-chloro-4-fluorophenyl)-6-methylpyrimidin-4-amine 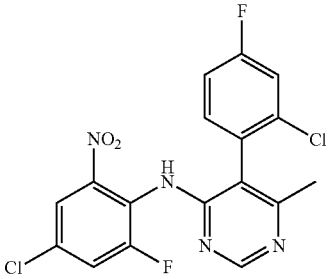 | LCMS (Method A): 3.97 min (411.0, MH$^+$). |
| AH | 2-Chloro-N-(4-chloro-2-fluoro-6-nitrophenyl)-3-(2-chloro-4-methoxyphenyl)pyridin-4-amine 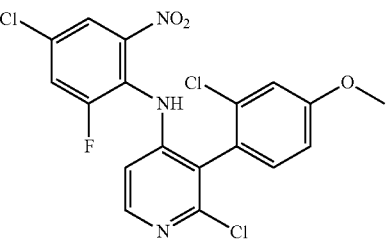 | (500 MHz, CDCl$_3$) δ 8.25 (s, 1H), 8.00-7.92 (m, 1H), 7.63 (s, 1H), 7.49 (ddd, J = 22.5, 9.8, 2.3 Hz, 1H), 7.18 (d, J = 2.5 Hz, 1H), 7.06 (dd, J = 8.4, 2.5 Hz, 1H), 6.59 (s, 1H), 3.91 (s, 3H). |

-continued

| Intermediate No. | Compound | ¹H NMR/LCMS |
|---|---|---|
| AI | 2-Chloro-N-(4-chloro-2-fluoro-6-nitrophenyl)-3-(2-chloro-4-fluorophenyl)pyridin-4-amine | (500 MHz, CDCl₃) δ 8.13 (d, J = 5.7 Hz, 1H), 7.92-7.81 (m, 1H), 7.51-7.37 (m, 2H), 7.29 (dt, J = 7.1, 4.7 Hz, 2H), 7.15 (td, J = 8.3, 2.6 Hz, 1H), 6.48 (t, J = 6.2 Hz, 1H). LCMS (Method A): 4.22 min (428.1, MH⁺). |
| AJ | 2-Chloro-3-(2-chloro-4-fluorophenyl)-N-(2-nitro-4-(prop-2-yn-1-yloxy)phenyl)pyridin-4-amine | (500 MHz, CDCl₃) δ 8.20 (d, J = 16.3 Hz, 1H), 8.14 (dd, J = 23.0, 5.7 Hz, 1H), 7.64 (d, J = 2.9 Hz, 1H), 7.55-7.47 (m, 1H), 7.33-7.24 (m, 2H), 7.25-7.18 (m, 1H), 7.15 (td, J = 8.5, 2.6 Hz, 2H), 4.67 (d, J = 2.4 Hz, 2H), 2.50 (t, J = 2.4 Hz, 1H). LCMS (Method A): 4.20 min (432.1, MH⁺). |
| AK | N-(4-Chloro-2-fluoro-6-nitrophenyl)-3-(2-chloro-4-fluorophenyl)-4-methylpyridin-2-amine | (500 MHz, CDCl₃) δ 8.10-8.04 (m, 1H), 7.83-7.79 (m, 1H), 7.32 (ddd, J = 10.8, 9.0, 2.4 Hz, 2H), 7.23 (dd, J = 8.5, 5.9 Hz, 1H), 7.17-7.11 (m, 1H), 6.93 (d, J = 5.5 Hz, 1H), 2.05 (s, 3H). LCMS (Method E): 2.16 min (410.1, MH⁺). |
| AL | 3-(2-Chloro-4-fluorophenyl)-4-methyl-N-(2-nitro-4-(prop-2-yn-1-yloxy)phenyl)pyridin-2-amine | LCMS (Method E): 2.31 min (412.2, MH⁺). |

-continued

| Intermediate No. | Compound | ¹H NMR/LCMS |
|---|---|---|
| AM | N-(4-Chloro-2-fluoro-6-nitrophenyl)-5-(2-chloro-4-fluorophenyl)-6-methylpyrimidin-4-amine | (500 MHz, CDCl$_3$) δ 8.55 (s, 1H), 7.82 (dd, J = 2.3, 1.9 Hz, 1H), 7.36 (ddd, J = 10.9, 8.9, 2.5 Hz, 2H), 7.29 (dd, J = 8.5, 5.9 Hz, 1H), 7.24 (s, 1H), 7.19-7.13 (m, 1H), 2.16 (s, 3H). LCMS (Method A): 3.36 min (411.0, MH$^+$). |
| AN | N-(4-Chloro-2-fluoro-6-nitrophenyl)-5-(2-chloro-4-methoxyphenyl)-6-methylpyrimidin-4-amine | (500 MHz, CDCl$_3$) δ 8.62 (s, 1H), 7.93-7.84 (m, 1H), 7.46 (dd, J = 9.4, 2.4 Hz, 1H), 7.42-7.35 (m, 1H), 7.19 (d, J = 2.5 Hz, 1H), 7.05 (dd, J = 8.6, 2.6 Hz, 1H), 3.91 (s, 3H). LCMS (Method A): 3.40 min (423.0, MH$^+$). |

Intermediates AO-BB:

The following Intermediates were prepared using the general method described for Intermediate N from the appropriate Intermediate.

| Intermediate No. | Compound | ¹H NMR/LCMS |
|---|---|---|
| AO | N$^1$-(2',6'-Difluoro-4'-methoxy-6-methyl-[1,1'-biphenyl]-2-yl)-4,6-difluorobenzene-1,2-diamine | LCMS (Method A): 4.15 min (377.1, MH$^+$). |

-continued
| Intermediate No. | Compound | $^1$H NMR/LCMS |
|---|---|---|
| AP | N$^1$-(2'-Chloro-4'-fluoro-6-methyl-[1,1'-biphenyl]-2-yl)benzene-1,2-diamine 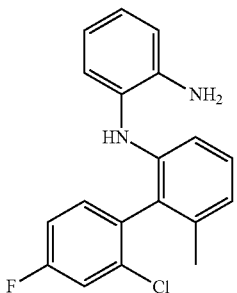 | LCMS (Method A): 4.29 min (327.2, MH$^+$). |
| AQ | 4-Chloro-N$^1$-(2'-chloro-4'-fluoro-6-methyl-[1,1'-biphenyl]-2-yl)benzene-1,2-diamine 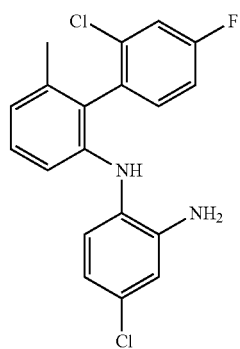 | LCMS (Method A): 4.48 min (361.0, MH$^+$). |
| AR | N$^1$-(2'-Chloro-4'-fluoro-6-methyl-[1,1'-biphenyl]-2-yl)-4-methylbenzene-1,2-diamine 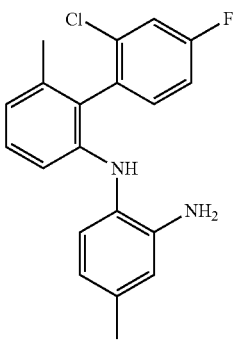 | LCMS (Method A): 4.45 min (341.2, MH$^+$). |

| Intermediate No. | Compound | ¹H NMR/LCMS |
| --- | --- | --- |
| AS | 4-Chloro-N¹-(5-(2-chloro-4-methoxyphenyl)-6-methylpyrimidin-4-yl)-6-fluorobenzene-1,2-diamine | LCMS (Method A): 3.58 min (393.1, MH⁺). |
| AT | 4-Chloro-N¹-(5-(2-chloro-4-fluorophenyl)-6-methylpyrimidin-4-yl)-6-fluorobenzene-1,2-diamine | LCMS (Method A): 3.56 min (381.1, MH⁺). |
| AU | 4-Chloro-N¹-(2-chloro-3-(2-chloro-4-methoxyphenyl)pyridin-4-yl)-6-fluorobenzene-1,2-diamine | LCMS (method A): 4.03 min (400.0, MH⁺). |
| AV | 4-Chloro-N¹-(2-chloro-3-(2-chloro-4-fluorophenyl)pyridin-4-yl)-6-fluorobenzene-1,2-diamine | LCMS (Method A): 4.20 min (402.0, MH⁺). |

-continued

| Intermediate No. | Compound | ¹H NMR/LCMS |
|---|---|---|
| AW | N¹-(2-Chloro-3-(2-chloro-4-fluorophenyl)pyridin-4-yl)-4-(prop-2-yn-1-yloxy)benzene-1,2-diamine | LCMS (Method A): 3.78 min (402.1, MH+). |
| AX | 5-Chloro-1-(3-(2-chloro-4-fluorophenyl)-4-methylpyridin-2-yl)-7-fluoro-1H-benzo[d]imidazole | LCMS (Method E): 2.10 min (380.1, MH+). |
| AY | N¹-(3-(2-Chloro-4-fluorophenyl)-4-methylpyridin-2-yl)-4-(prop-2-yn-1-yloxy)benzene-1,2-diamine | LCMS (method E): 1.99 min (382.2, MH+). |
| AZ | 4-Chloro-N¹-(5-(2-chloro-4-fluorophenyl)-6-methylpyrimidin-4-yl)-6-fluorobenzene-1,2-diamine | (500 MHz, CDCl₃) δ 8.55 (s, 1H), 7.82 (dd, J = 2.3, 1.9 Hz, 1H), 7.36 (ddd, J = 10.9, 8.9, 2.5 Hz, 2H), 7.29 (dd, J = 8.5, 5.9 Hz, 1H), 7.24 (s, 1H), 7.19-7.13 (m, 1H), 2.16 (s, 3H). LCMS (Method A): 3.36 min (411.0, MH+). |

| Intermediate No. | Compound | ¹H NMR/LCMS |
|---|---|---|
| BA | 4-Chloro-N¹-(5-(2-chloro-4-methoxyphenyl)-6-methylpyrimidin-4-yl)-6-fluorobenzene-1,2-diamine | (500 MHz, CDCl$_3$) δ 8.62 (s, 1H), 7.93-7.84 (m, 1H), 7.46 (dd, J = 9.4, 2.4 Hz, 1H), 7.42-7.35 (m, 1H), 7.19 (d, J = 2.5 Hz, 1H), 7.05 (dd, J = 8.6, 2.6 Hz, 1H), 3.91 (s, 3H). LCMS (method A): 3.40 min (423.0, MH$^+$). |
| BB | 4-Chloro-N¹-(5-(2,6-difluoro-4-methoxyphenyl)-6-methylpyrimidin-4-yl)-6-fluorobenzene-1,2-diamine | (500 MHz, DMSO-d$^6$) δ 8.33 (s, 1H), 7.77 (s, 1H), 6.92 (d, J = 9.8 Hz, 2H), 6.58 (s, 1H), 6.50 (d, J = 8.7 Hz, 1H), 5.19 (s, 2H), 3.84 (s, 3H), 2.07 (s, 3H). |

Intermediate BC

The following Intermediate was prepared using the general method described for Intermediate B from 5,6-dichloropyridazin-4-amine and 2-chloro-4-fluorophenylboronic acid.

| Intermediate No. | Compound | ¹H NMR/LCMS |
|---|---|---|
| BC | 6-Chloro-5-(2-chloro-4-fluorophenyl)pyridazin-4-amine | LCMS (Method A): 2.41 min (258.1, MH$^+$). |

Intermediate BD

The following Intermediate was prepared using the general method described for Intermediate H from the appropriate Intermediate (BC) and 2,5-difluoronitrobenzene.

| Intermediate No. | Compound | ¹H NMR/LCMS |
|---|---|---|
| BD | 6-Chloro-5-(2-chloro-4-fluorophenyl)-N-(4-fluoro-2-nitrophenyl)pyridazin-4-amine 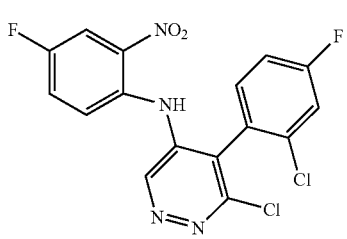 | LCMS (Method A): 3.69 min (397.1, MH$^+$). |

Intermediate BE

The following Intermediate was prepared using the general method described for Intermediate N from the appropriate Intermediate BD.

| Intermediate No. | Compound | ¹H NMR/LCMS |
|---|---|---|
| BE | N$^1$-(6-Chloro-5-(2-chloro-4-fluorophenyl)pyridazin-4-yl)-4-fluorobenzene-1,2-diamine 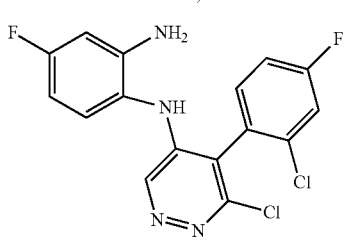 | LCMS (Method A): 3.35 min (367.1, MH$^+$). |

Example 1: 1-(5-(2-Chloro-4-fluorophenyl)-6-methylpyrimidin-4-yl)-5,7-difluoro-1H-benzo[d]imidazole

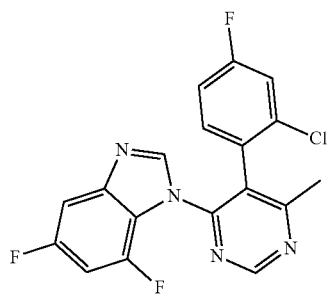 [SMILES: Cc1ncnc(-n2cnc3cc(F)cc(F)c32)c1-c1ccc(F)cc1Cl]

Concentrated HCl (2.0 µl, 16 µmol) was added to a solution of Intermediate L (116 mg, 0.318 mmol) in trimethylorthoformate (522 µl, 4.77 mmol), and the mixture was stirred at 100° C. for 3 h. After cooling to room temperature, the reaction mixture was partitioned between water and EtOAc. The aqueous layer was extracted with EtOAc (×3). The combined organic phases were washed with brine, dried (MgSO$_4$) and concentrated in vacuo. The residue was purified by chromatography (SiO$_2$, 0-60% EtOAc in PE) and the title compound was isolated as a pale orange solid (94 mg, 79%). ¹H NMR δ$_H$ (500 MHz, CDCl$_3$) 9.18 (s, 1H), 7.62 (s, 1H), 7.26-7.16 (m, 3H), 7.03 (td, J=8.2, 2.5 Hz, 1H), 6.91-6.82 (m, 1H), 2.48 (s, 3H). LCMS (Method A): 3.15 min (375.2, MH$^+$).

Examples 2-6

The following Examples were prepared using the general method described in Example 1 from Intermediates O-S.

| Example No. | Compound | ¹H NMR/LCMS |
|---|---|---|
| 2 | 1-(5-(2-Chloro-4-methoxyphenyl)-6-methylpyrimidin-4-yl)-5,7-difluoro-1H-benzo[d]imidazole | (500 MHz, CDCl$_3$) δ 9.15 (s, 1H), 7.62 (s, 1H), 7.24 (dd, J = 8.3, 2.0 Hz, 1H), 7.07 (d, J = 8.6 Hz, 1H), 6.98 (d, J = 2.5 Hz, 1H), 6.90-6.84 (m, 1H), 6.81 (dd, J = 8.6, 2.6 Hz, 1H), 3.80 (s, 3H), 2.48 (s, 3H). LCMS (Method A): 3.16 min (387.2, MH$^+$). |
| 3 | 1-(5-(2-Chlorophenyl)-6-methylpyrimidin-4-yl)-5,7-difluoro-1H-benzo[d]imidazole | (500 MHz, CDCl$_3$) δ 9.18 (s, 1H), 7.61 (s, 1H), 7.46 (dd, J = 8.0, 1.0 Hz, 1H), 7.35 (td, J = 7.8, 1.7 Hz, 1H), 7.29 (td, J = 7.5, 1.3 Hz, 1H), 7.25-7.22 (m, 1H), 7.19 (dd, J = 7.6, 1.7 Hz, 1H), 6.90-6.83 (m, 1H), 2.48 (s, 3H). LCMS (Method A): 3.10 min (357.2, MH$^+$). |
| 4 | 1-(3-(2-Chloro-4-fluorophenyl)-4-methylpyridin-2-yl)-5,7-difluoro-1H-benzo[d]imidazole | (500 MHz, CDCl$_3$) δ 8.56 (d, J = 5.0 Hz, 1H), 7.73 (s, 1H), 7.44 (d, J = 5.0 Hz, 1H), 7.21 (dd, J = 8.7, 2.1 Hz, 1H), 7.14 (dd, J = 8.3, 2.5 Hz, 1H), 7.09 (dd, J = 8.5, 5.9 Hz, 1H), 6.90 (td, J = 8.2, 2.5 Hz, 1H), 6.83-6.75 (m, 1H), 2.22 (s, 3H). LCMS (Method A): 3.27 min (374.3, MH$^+$). |
| 5 | 1-(2-Chloro-3-(2-chloro-4-fluorophenyl)pyridin-4-yl)-5,7-difluoro-1H-benzo[d]imidazole | (500 MHz, CDCl$_3$) δ 8.66 (d, J = 5.3 Hz, 1H), 7.59 (s, 1H), 7.44 (dd, J = 5.2, 3.3 Hz, 1H), 7.26-7.22 (m, 1H), 7.16 (br m, 2H), 6.97 (br m, 1H), 6.91-6.81 (m, 1H). LCMS (Method A): 3.38 min (394.1, MH$^+$). |

| Example No. | Compound | ¹H NMR/LCMS |
|---|---|---|
| 6 | 1-(2'-Chloro-4'-fluoro-6-methyl-[1,1'-biphenyl]-2-yl)-5,7-difluoro-1H-benzo[d]imidazole | (500 MHz, CDCl$_3$) δ 7.86 (br s, 1H), 7.54-7.49 (m, 2H), 7.41-7.35 (m, 1H), 7.27 (dd, J = 8.7, 1.7 Hz, 1H), 7.18-7.10 (br m, 1H), 7.00-6.93 (br m, 1H), 6.86-6.70 (m, 2H), 2.16 (s, 3H). LCMS (Method A): 4.12 min (373.1, MH$^+$). |

Examples 7-19

The following Examples were prepared using the general method described in Example 1 from Intermediates AO-BB.

| Example No. | Compound | ¹H NMR/LCMS |
|---|---|---|
| 7 | 1-(2',6'-Difluoro-4'-methoxy-6-methyl-[1,1'-biphenyl]-2-yl)-5,7-difluoro-1H-benzo[d]imidazole | (500 MHz, CDCl$_3$) δ 7.68 (s, 1H), 7.51-7.47 (m, 2H), 7.36-7.33 (m, 1H), 7.21 (dd, J = 8.7, 1.8 Hz, 1H), 6.77-6.71 (m, 1H), 6.40 (m, 1H), 6.24 (m, 1H), 3.70 (s, 3H), 2.24 (s, 3H). LCMS (Method A): 3.95 min (387.2, MH$^+$). |
| 8 | 1-(2'-Chloro-4'-fluoro-6-methyl-[1,1'-biphenyl]-2-yl)-1H-benzo[d]imidazole | (500 MHz, CDCl$_3$) δ 7.71 (dd, J = 6.2, 2.8 Hz, 1H), 7.68 (s, 1H), 7.48 (ddd, J = 8.4, 7.7, 4.2 Hz, 2H), 7.35 (dd, J = 7.6, 0.8 Hz, 1H), 7.27-7.23 (m, 3H), 7.08 (dd, J = 8.3, 2.3 Hz, 1H), 6.93-6.84 (m, 1H), 6.74 (t, J = 7.1 Hz, 1H), 2.16 (s, 3H). LCMS (Method A): 3.86 min (337.3, MH$^+$). |
| 9 | 5-Chloro-1-(2'-chloro-4'-fluoro-6-methyl-[1,1'-biphenyl]-2-yl)-1H-benzo[d]imidazole | (500 MHz, CDCl$_3$) δ 7.71-7.67 (m, 2H), 7.53-7.46 (m, 2H), 7.34-7.30 (m, 1H), 7.19 (qd, J = 8.6, 1.1 Hz, 2H), 7.09 (m, 1H), 6.88 (m, 1H), 6.77 (m, 1H), 2.16 (s, 3H). LCMS (Method A): 4.25 min (371.0, MH$^+$). |

-continued

| Example No. | Compound | ¹H NMR/LCMS |
|---|---|---|
| 10 | 1-(2'-Chloro-4'-fluoro-6-methyl-[1,1'-biphenyl]-2-yl)-5-methyl-1H-benzo[d]imidazole | (500 MHz, CDCl$_3$) δ 7.61 (s, 1H), 7.47 (m, 3H), 7.34 (d, J = 7.5 Hz, 1H), 7.16 (d, J = 8.2 Hz, 1H), 7.08 (m, 2H), 6.89 (m, 1H), 6.75 (m, 1H), 2.46 (s, 3H), 2.16 (s, 3H). LCMS (Method A): 4.32 min (351.4, MH$^+$). |
| 11 | 5-Chloro-1-(5-(2-chloro-4-methoxyphenyl)-6-methylpyrimidin-4-yl)-7-fluoro-1H-benzo[d]imidazole | (500 MHz, CDCl$_3$) δ 9.15 (s, 1H), 7.61 (s, 1H), 7.54 (d, J = 1.7 Hz, 1H), 7.07 (m, 2H), 6.97 (d, J = 2.5 Hz, 1H), 6.80 (dd, J = 8.6, 2.6 Hz, 1H), 3.79 (s, 3H), 2.48 (s, 3H), 1.59 (s, 3H). LCMS (Method A): 4.07 min (403.1, MH$^+$). |
| 12 | 5-Chloro-1-(5-(2-chloro-4-fluorophenyl)-6-methylpyrimidin-4-yl)-7-fluoro-1H-benzo[d]imidazole | (500 MHz, CDCl$_3$) δ 9.18 (s, 1H), 7.61 (s, 1H), 7.54 (d, J = 1.7 Hz, 1H), 7.20 (m, 2H), 7.07 (dd, J = 10.4, 1.6 Hz, 1H) 7.02 (ddd J = 8.6, 7.8, 2.6 Hz, 1H), 2.47 (s, 3H). LCMS (Method A): 4.03 min (391.1, MH$^+$). |
| 13 | 5-Chloro-1-(2-chloro-3-(2-chloro-4-methoxyphenyl)pyridin-4-yl)-7-fluoro-1H-benzo[d]imidazole | (500 MHz, CDCl$_3$) δ 8.63 (d, J = 4.3 Hz, 1H), 8.05 (s, 1H), 7.68 (s, 1H), 7.43 (s, 1H), 7.13 (d, J = 10.5 Hz, 1H), 7.02 (s, 1H), 6.84 (d, J = 2.1 Hz, 1H), 6.72 (s, 1H), 3.72 (s, 3H). LCMS (Method A): 4.14 mins (424.0, MH$^+$). |
| 14 | 5-Chloro-1-(2-chloro-3-(2-chloro-4-fluorophenyl)pyridin-4-yl)-7-fluoro-1H-benzo[d]imidazole | (500 MHz, CDCl$_3$) δ 8.62 (d, J = 5.0 Hz, 1H), 7.86 (s, 1H), 7.55 (d, J = 1.3 Hz, 1H), 7.43 (d, J = 1.7 Hz, 1H), 7.15 (d, J = 9.3 Hz, 1H), 7.06 (ddd, J = 12.0, 9.4, 1.8 Hz, 2H), 6.91 (s, 1H). LCMS (Method A): 4.17 min (412.0, MH$^+$). |

-continued

| Example No. | Compound | ¹H NMR/LCMS |
|---|---|---|
| 15 | 1-(2-Chloro-3-(2-chloro-4-fluorophenyl)pyridin-4-yl)-5-(prop-2-yn-1-yloxy)-1H-benzo[d]imidazole<br />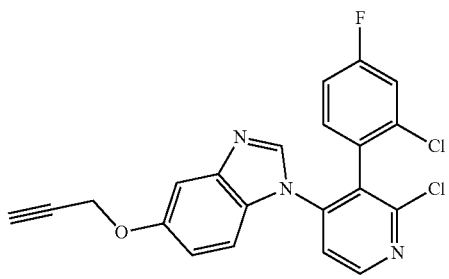 | (500 MHz, CDCl₃) δ 8.67 (d, J = 4.7 Hz, 1H), 8.30 (s, 1H), 7.51 (d, J = 4.6 Hz, 1H), 7.36 (d, J = 1.9 Hz, 1H), 7.23 (d, J = 9.0 Hz, 1H), 7.18-7.12 (m, 1H), 7.07 (ddd, J = 22.1, 8.6, 2.3 Hz, 2H), 6.96-6.86 (m, 1H), 4.68 (d, J = 2.4 Hz, 2H), 2.49 (t, J = 2.3 Hz, 1H). LCMS (Method A): 3.68 min (412.1, MH⁺). |
| 16 | 5-Chloro-1-(3-(2-chloro-4-fluorophenyl)-4-methylpyridin-2-yl)-7-fluoro-1H-benzo[d]imidazole<br />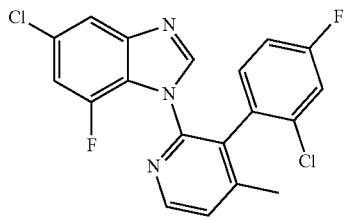 | (500 MHz, CDCl₃) δ 8.51 (d, J = 5.0 Hz, 1H), 8.21 (s, 1H), 7.65 (s, 1H), 7.45 (d, J = 4.9 Hz, 1H), 7.15-7.01 (m, 3H), 6.89 (dd, J = 7.8, 6.0 Hz, 1H), 2.16 (s, 3H). LCMS (Method A): 4.13 min (390.1, MH⁺). |
| 17 | 1-(3-(2-Chloro-4-fluorophenyl)-4-methylpyridin-2-yl)-5-(prop-2-yn-1-yloxy)-1H-benzo[d]imidazole<br />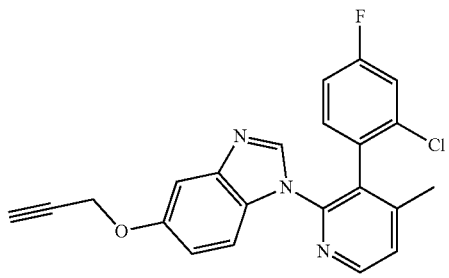 | (500 MHz, CDCl₃) δ 8.55 (d, J = 4.8 Hz, 1H), 8.14 (s, 1H), 7.50-7.41 (m, 2H), 7.39 (s, 1H), 7.14 (d, J = 7.7 Hz, 1H), 7.10-6.98 (m, 2H), 6.92 (s, 1H), 4.69 (d, J = 2.3 Hz, 2H), 2.49 (s, 1H), 2.18 (s, 3H). LCMS (Method A): 3.76 min (392.1, MH⁺). |
| 18 | 5-Bromo-1-(2-chloro-3-(2-chloro-4-methoxyphenyl)pyridin-4-yl)-7-fluoro-1H-benzo[d]imidazole<br />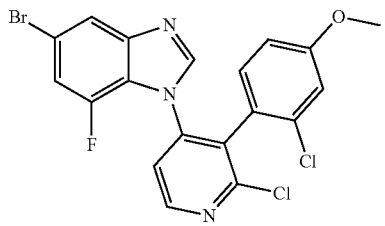 | (500 MHz, CDCl₃) δ 8.55 (d, J = 5.3 Hz, 1H), 7.64 (d, J = 1.4 Hz, 1H), 7.50 (s, 1H), 7.33 (dd, J = 5.2, 3.6 Hz, 1H), 7.14 (dd, J = 10.4, 1.4 Hz, 1H), 6.98 (s, 1H), 6.84 (d, J = 2.4 Hz, 1H), 6.69 (d, J = 8.2 Hz, 1H), 3.71 (s, 3H). LCMS (Method E): 2.14 min (467.9, MH⁺). |

| Example No. | Compound | ¹H NMR/LCMS |
|---|---|---|
| 19 | 5-Chloro-1-(5-(2,6-difluoro-4-methoxyphenyl)-6-methylpyrimidin-4-yl)-7-fluoro-1H-benzo[d]imidazole<br>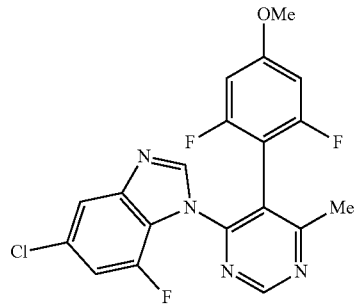 | (500 MHz, DMSO-d⁶) δ 9.29 (s, 1H), 8.25 (s, 1H), 7.69 (s, 1H), 7.36 (d, J = 10.8 Hz, 1H), 6.82 (d, J = 10.4 Hz, 2H), 3.75 (s, 6H). LCMS (Method F): 2.03 min (405.0, MH⁺). |

Example 20: 5-Chloro-1-(2-chloro-3-(2-chloro-4-methoxyphenyl)pyridin-4-yl)-7-fluoro-1H-benzo[d][1,2,3]triazole

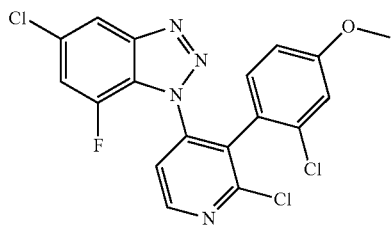 [SMILES: COc1ccc(-c2c(-n3nnc4cc(Cl)cc(F)c43)ccnc2Cl)c(Cl)c1]

Hydrochloric acid (3 M, 3 mL) was added to Intermediate AU (0.112 g, 0.271 mmol) and the mixture sonicated until the it was a suspension. A solution of sodium nitrite (0.028 g, 0.41 mmol) in water (0.25 mL) was then added dropwise and the reaction mixture stirred at r.t. for 1 hr. The reaction mixture was then diluted with EtOAc and water and the phases separated. The reaction mixture was then dried (MgSO₄) and concentrated in vacuo to give the title compound as an orange solid (91 mg, 79%). ¹H NMR (500 MHz, DMSO-d⁶) δ$_H$ 8.84 (d, J=5.2 Hz, 1H), 8.18 (d, J=1.6 Hz, 1H), 8.09 (dd, J=5.2, 2.8 Hz, 1H), 7.80 (dd, J=10.2, 1.5 Hz, 1H), 7.29 (d, J=8.6 Hz, 1H), 6.99 (d, J=2.5 Hz, 1H), 6.89 (dd, J=8.6, 2.5 Hz, 1H), 3.74 (s, 3H).

Examples 21-26

The following Examples were prepared using the general method described in Example 20 from the appropriate Intermediate.

| Example No. | Compound | ¹H NMR/LCMS |
|---|---|---|
| 21 | 5-Chloro-1-(5-(2-chloro-4-fluorophenyl)-6-methylpyrimidin-4-yl)-7-fluoro-1H-benzo[d][1,2,3]triazole<br>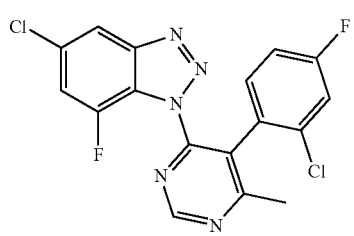 | (500 MHz, CDCl₃) δ 9.15 (s, 1H), 7.77 (s, 1H), 7.27 (ddd, J = 22.9, 15.1, 7.0 Hz, 2H), 7.05 (dd, J = 8.3, 2.4 Hz, 1H), 6.98 (td, J = 8.4, 2.4 Hz, 1H), 2.44 (s, 3H). LCMS (Method A): 3.89 min (392.0, MH⁺). |

-continued

| Example No. | Compound | $^1$H NMR/LCMS |
|---|---|---|
| 22 | 5-Chloro-1-(5-(2-chloro-4-methoxyphenyl)-6-methylpyrimidin-4-yl)-7-fluoro-1H-benzo[d][1,2,3]triazole | (500 MHz, CDCl$_3$) δ 9.22 (s, 1H), 7.85 (d, J = 1.5 Hz, 1H), 7.30 (dd, J = 9.4, 1.6 Hz, 1H), 7.25 (d, J = 8.5 Hz, 1H), 6.91-6.83 (m, 2H), 3.80 (s, 3H), 2.54 (s, 3H). LCMS (Method A): 3.80 min (404.0, MH$^+$). |
| 23 | 5-Chloro-1-(3-(2-chloro-4-fluorophenyl)-4-methylpyridin-2-yl)-7-fluoro-1H-benzo[d][1,2,3]triazole | (500 MHz, CDCl$_3$) δ 8.61 (d, J = 5.0 Hz, 1H), 7.82 (d, J = 1.5 Hz, 1H), 7.53 (dd, J = 5.0, 0.6 Hz, 1H), 7.34-7.29 (m, 1H), 7.23 (dd, J = 9.5, 1.5 Hz, 1H), 7.05 (dd, J = 8.4, 2.5 Hz, 1H), 7.01-6.95 (m, 1H), 2.28 (s, 3H). LCMS (Method A): 3.88 min (391.0 MH$^+$). |
| 24 | 5-Chloro-1-(3-(2-chloro-4-methoxyphenyl)-4-methylpyridin-2-yl)-7-fluoro-1H-benzo[d][1,2,3]triazole | (500 MHz, CDCl$_3$) δ 8.49 (d, J = 5.0 Hz, 1H), 7.72 (d, J = 1.5 Hz, 1H), 7.42 (dd, J = 5.0, 0.6 Hz, 1H), 7.13-7.08 (m, 2H), 6.72 (d, J = 2.5 Hz, 1H), 6.67 (dd, J = 8.5, 2.6 Hz, 1H), 3.67 (s, 3H), 2.20 (s, 3H). LCMS (Method A): 3.81 min (403.0, MH$^+$). |
| 25 | 5-Chloro-1-(2-chloro-3-(2-chloro-4-fluorophenyl)pyridin-4-yl)-7-fluoro-1H-benzo[d][1,2,3]triazole | (500 MHz, CDCl$_3$) δ 8.66 (d, J = 5.2 Hz, 1H), 7.77 (d, J = 1.4 Hz, 1H), 7.39 (dd, J = 5.2, 2.9 Hz, 1H), 7.26 (dd, J = 8.6, 5.8 Hz, 1H), 7.22-7.16 (m, 1H), 7.01-6.84 (m, 2H). LCMS (Method A): 3.89 min (410.9, MH$^+$). |
| 26 | 5-Bromo-1-(2-chloro-3-(2-chloro-4-methoxyphenyl)pyridin-4-yl)-7-fluoro-1H-benzo[d][1,2,3]triazole | (500 MHz, CDCl$_3$) δ 8.62 (d, J = 5.2 Hz, 1H), 7.93 (s, 1H), 7.37 (dd, J = 5.0, 2.4 Hz, 1H), 7.29 (d, J = 9.4 Hz, 1H), 7.15 (d, J = 9.2 Hz, 1H), 6.73-6.62 (m, 2H), 5.23 (s, 1H), 3.68 (s, 3H). LCMS (Method A): 3.88 min (468.9, MH$^+$). |

Example 27

The following Example was prepared using the general method described in Example 1 from Intermediate BE.

| Example No. | Compound | ¹H NMR/LCMS |
|---|---|---|
| 27 | 1-(6-Chloro-5-(2-chloro-4-fluorophenyl)pyridazin-4-yl)-5-fluoro-1H-benzo[d]imidazole 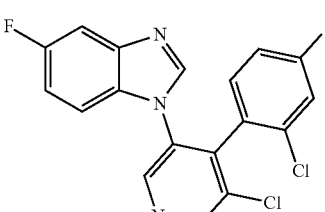 | (500 MHz, DMSO-d$^6$) δ 9.74 (s, 1H), 8.74 (s, 1H), 7.80 (dd, J = 8.6, 6.1 Hz, 1H), 7.76 (dd, J = 8.9, 2.5 Hz, 1H), 7.69 (dd, J = 9.4, 2.4 Hz, 1H), 7.51 (m, 2H), 7.28 (td, J = 9.2, 2.5 Hz, 1H). LCMS (Method A): 3.66 min (377.1, MH⁺). |

Example 28: Testing the Fungicidal Activity of the Compounds of the Invention Compounds were screened in 96 well plates with 10 compounds per plate. Each compound was screened using agar amended to 20, 2, 0.2 and 0.02 ppm of the test material. Proline at 50 and 10 ppm and 0.2% DMSO were used respectively as positive and negative controls. Each test concentration and standard were tested twice on a plate.

Compounds were screened against the following three fungal pathogens—*Botrytis cinerea*, *Alternaria alternata* and *Zymoseptoria tritici*. The agar used in the test varied depending on the pathogen with Medium N used for *B. cinerea* and *A. alternata* and 1% potato dextrose agar for *Z. tritici*. For each pathogen sufficient spores were added to the appropriate agar to give 1,000 spores/ml agar of *A. alternata*, 5,000 spores/ml agar of *B. cinerea* and 10,000 spores/ml agar of *Z. tritici*.

A ×10 stock solution in 2% DMSO was produced for each dose i.e. 200, 20, 2 and 0.2 ppm, and 10 µl of this added to the appropriate wells on the plate. An equivalent amount of 2% DMSO and Proline stock at 500 and 100 ppm were added for the controls. To each well 90 µl of the appropriate agar spore suspension was added to give the final well concentrations outlined in the first paragraph.

Plates were incubated at room temperature (18° C.) and assessed after
a) 3 to 4 days *A. alternata* and *B. cinerea*
b) 7 days for *Z. tritici*

The amount of fungal growth in each well was compared to the DMSO controls and scored according to the following key
- 0—no growth (100% control)
- 1—growth reduced by 75% compared to DMSO control (25% growth)
- 2—growth reduced by 50% compared to DMSO control (50% growth)
- 3—growth reduced by 25% compared to DMSO control growth (75% growth)
- 4—no reduction in growth compared to DMSO control growth (100% growth)

Those numbers were then used to give an EC50. The ranking in the table is:

A) EC50<20 ppm, B) EC50≥20ppm

| Example | Botrytis | Alternaria | Zymoseptoria |
|---|---|---|---|
| 1 | A | A | A |
| 2 | A | A | A |
| 3 | A | A | A |
| 4 | A | A | A |
| 5 | A | A | A |
| 6 | A | A | A |
| 7 | A | A | A |
| 8 | A | A | A |
| 9 | A | A | A |
| 10 | A | A | A |
| 11 | A | A | A |
| 12 | A | A | A |
| 13 | A | A | A |
| 14 | A | A | A |
| 15 | A | A | A |
| 16 | A | A | A |
| 17 | A | A | A |
| 18 | A | A | A |
| 19 | A | A | A |
| 20 | A | A | A |
| 21 | A | B | A |
| 22 | A | B | A |
| 23 | A | A | A |
| 24 | A | B | A |
| 25 | A | A | A |
| 26 | A | B | B |
| 27 | A | B | A |

The invention claimed is:

1. A compound of formula I, or an agronomically acceptable salt or N-oxide thereof:

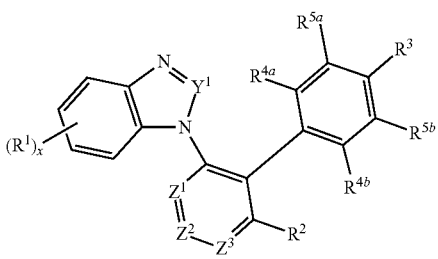

I $Y^1$ is selected from CH and N;

$Z^1$, $Z^2$ and $Z^3$ are each independently selected from N and $CR^6$; wherein at least one of $Z^1$, $Z^2$ and $Z^3$ is $CR^6$;

$R^1$ and $R^{10}$ are each independently at each occurrence selected from: $C_1$-$C_6$-alkyl, $C_1$-$C_6$-haloalkyl, $C_3$-$C_6$-cycloalkyl, halo, nitro, $OR^7$, $SR^8$, $OS(O)_2R^8$, $S(O)_2R^8$, $C(O)OR^8$, $C(O)NR^8R^8$, $C(O)R^8$, $S(O)_2NR^8R^8$, $S(O)(NR^8)R^8$, $S(O)R^8$, cyano, $C_2$-$C_6$-alkenyl, $C_2$-$C_6$-alkynyl, and $NR^8R^9$;

$R^2$ and $R^6$ are each independently at each occurrence selected from H, halo, nitro, cyano, $C_1$-$C_6$-alkyl, $C_3$-$C_6$-cycloalkyl and $C_1$-$C_6$-haloalkyl;

$R^3$, $R^{5a}$ and $R^{5b}$ are independently at each occurrence selected from H, $C_1$-$C_6$-alkyl, $C_1$-$C_6$-haloalkyl, $C_3$-$C_6$-cycloalkyl, halo, nitro, $OR^7$, $SR^8$, $OS(O)_2R^8$, $S(O)_2R^8$, $C(O)OR^8$, $C(O)NR^8R^8$, $C(O)R^8$, $S(O)_2NR^8R^8$, $S(O)(NR^8)R^8$, $S(O)R^8$, cyano, $C_2$-$C_6$-alkenyl, $C_2$-$C_6$-alkynyl, and $NR^8R^9$;

$R^{4a}$ and $R^{4b}$ are independently at each occurrence selected from H, $C_1$-$C_6$-alkyl, $C_1$-$C_6$-haloalkyl, $C_3$-$C_6$-cycloalkyl, halo, nitro, $SR^8$, $OS(O)_2R^8$, $S(O)_2R^8$, $C(O)OR^8$, $C(O)NR^8R^8$, $C(O)R^8$, $S(O)_2NR^8R^8$, $S(O)(NR^8)R^8$, $S(O)R^8$, cyano, C2-C6-alkenyl, C2-C6-alkynyl, or wherein $R^{4b}$ and $R^{5b}$ together with the carbon atoms to which they are attached together form a ring selected from: phenyl, 5- or 6-membered heteroaryl, 5-, 6- or 7-membered heterocycloalkyl ring and $C_5$-$C_7$-cycloalkyl; said heteroaryl or phenyl ring being optionally substituted with from 1 to 4 $R^{10}$ groups or said heterocycloalkyl or cycloalkyl ring being optionally substituted with from 1 to 4 $R^{11}$ groups;

with the proviso that either at least one of $R^{4a}$ and $R^{4b}$ is selected from $C_1$-$C_6$-alkyl, $C_1$-$C_6$-haloalkyl, halo, nitro, $SR^8$, $OS(O)_2R^8$, $S(O)_2R^8$, $S(O)_2NR^8R^8$, $S(O)(NR^8)R^8$, $S(O)R^8$, cyano, $C_2$-$C_6$-alkenyl, and $C_2$-$C_6$-alkynyl or $R^{4b}$ and $R^{5b}$ together form a ring;

$R^7$ is independently at each occurrence selected from: H, $C_1$-$C_6$-alkyl, $C_3$-$C_6$-alkenyl, $C_3$-$C_6$-alkynyl, $C_3$-$C_6$-cycloalkyl and $C_1$-$C_6$-haloalkyl;

$R^8$ is independently at each occurrence selected from: H, $C_3$-$C_6$-cycloalkyl and $C_1$-$C_6$-alkyl;

or where two $R^8$ groups are attached to the same nitrogen atom, said $R^8$ groups, together with said nitrogen atom form a 4-, 5-, 6- or 7-membered heterocycloalkyl ring;

$R^9$ is independently at each occurrence selected from; H, $C_1$-$C_6$-alkyl, $C(O)$—$C_1$-$C_6$-alkyl and $S(O)_2$—$C_1$-$C_6$-alkyl;

or where an $R^8$ group and an $R^9$ group are attached to the same nitrogen atom, said $R^8$ and $R^9$ groups, together with said nitrogen atom form a 4-, 5-, 6- or 7-membered heterocycloalkyl ring;

$R^{11}$ is independently at each occurrence selected from: =O, =S, $C_1$-$C_6$-alkyl, $C_1$-$C_6$-haloalkyl, halo, nitro, $OR^8$, $SR^8$, $OS(O)_2R^8$, $S(O)_2R^8$, $S(O)_2NR^8R^8$, $S(O)(NR^8)R^8$, $S(O)R^8$, cyano, $C_2$-$C_6$-alkenyl, $C_2$-$C_6$-alkynyl, and $NR^8R^9$; and x is an integer from 0 to 4;wherein for any $R^1$, $R^2$, $R^3$, $R^{4a}$, $R^{4b}$, $R^{5a}$, $R^{5b}$, $R^6$, $R^7$, $R^8$, $R^9$, $R^{10}$, or $R^{11}$ group that is alkyl, alkenyl, cycloalkyl, heterocycloalkyl (including where two $R^8$ groups or an $R^8$ group and an $R^9$ group together with a nitrogen to which they are attached form a heterocycloalkyl ring), alkynyl, C(O)-alkyl or $S(O)_2$-alkyl is optionally substituted, where chemically possible, by 1 to 4 substituents which are each independently selected at each occurrence from the group consisting of: =O; =$NR^a$, =$NOR^a$, $C_1$-$C_4$-alkyl, halo, nitro, cyano, $C_1$-$C_4$-haloalkyl, $C_2$-$C_4$-alkenyl, $C_2$-$C_4$-alkynyl, $NR^aR^b$, $S(O)_2R^a$, $S(O)R^a$, $S(O)(NR^a)R^a$, $S(O)_2NR^aR^a$, $CO_2R^a$, $C(O)R^a$, $CONR^aR^a$ and $OR^a$;

wherein $R^a$ is independently selected from H and $C_1$-$C_4$-alkyl; and $R^b$ is independently H, $C_1$-$C_4$-alkyl, C(O)—$C_1$-$C_4$-alkyl, $S(O)_2$—$C_1$-$C_4$-alkyl.

2. A compound of claim 1, wherein $Y^1$ is CH.

3. A compound of claim 1, wherein $Y^1$ is N.

4. A compound of claim 1, wherein $Z^2$ is $CR^6$.

5. A compound of claim 1, wherein $Z^1$ and $Z^3$ are each N.

6. A compound of claim 1, wherein $Z^1$ is $CR^6$ and $Z^3$ is N.

7. A compound of claim 1, wherein $Z^3$ is $CR^6$ and $Z^1$ is N.

8. A compound of claim 1, wherein $Z^1$ and $Z^3$ are each $CR^6$.

9. A compound of claim 1, wherein x is an integer selected from 1 and 2 and $R^1$ is independently at each occurrence selected from $C_1$-$C_4$-alkyl, $C_1$-$C_4$-haloalkyl, halo, nitro, $OR^7$, and cyano.

10. A compound of claim 1, wherein $R^2$ is independently selected from $C_1$-$C_2$-alkyl and $C_1$-$C_2$-haloalkyl.

11. A compound of claim 1, wherein $R^{4a}$ is independently selected from halo, $C_1$-$C_4$-alkyl, and $C_1$-$C_4$-haloalkyl.

12. A compound of claim 1, wherein $R^{4b}$ is independently selected from halo, $C_1$-$C_4$-alkyl, and $C_1$-$C_4$-haloalkyl.

13. A compound of claim 1, wherein neither $R^{4a}$ nor $R^{4b}$ are H.

14. A compound of claim 1, wherein $R^{4b}$ is H.

15. A compound of claim 1, wherein $R^{5a}$ is H.

16. A compound of claim 1, wherein $R^{5b}$ is H.

17. A compound of claim 1, wherein $R^3$ is independently selected from halo, $C_1$-$C_4$-alkyl, $C_1$-$C_4$-haloalkyl, O—$C_1$-$C_4$-alkyl and O—$C_1$-$C_4$-haloalkyl.

18. A compound of claim 1, wherein the compound of formula (I) is selected from:

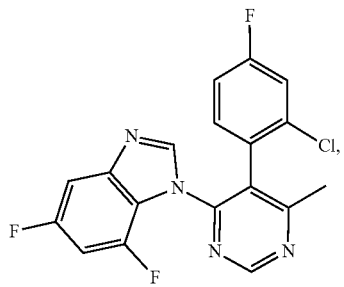

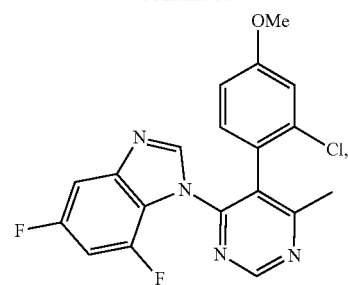
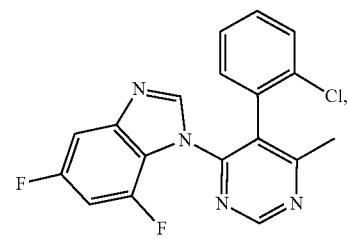
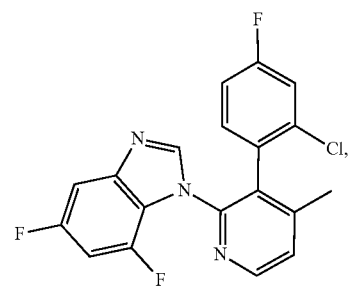
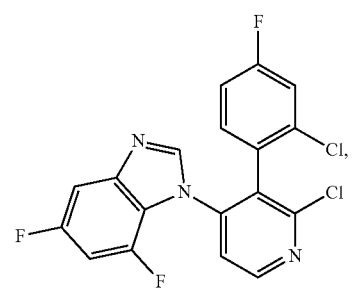
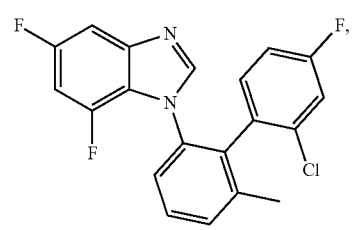
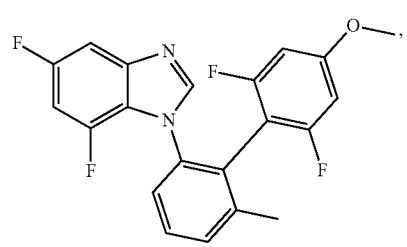
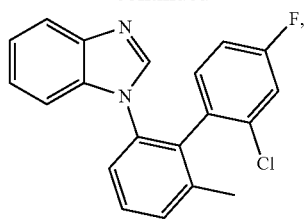
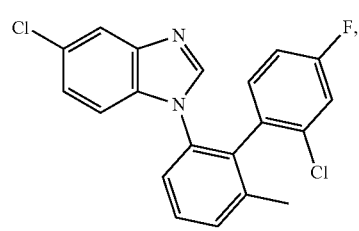
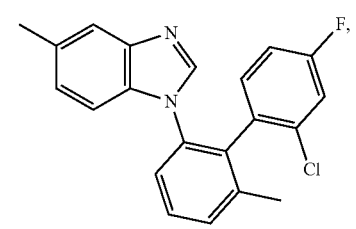
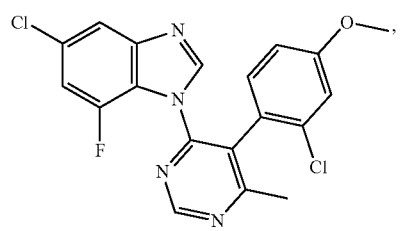
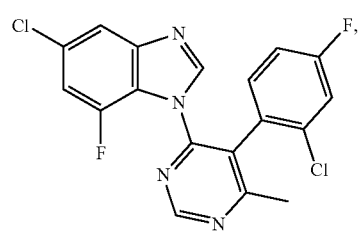
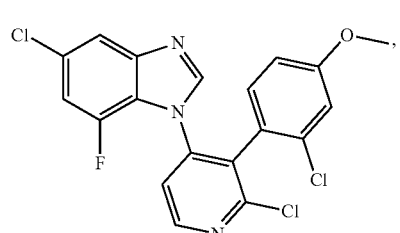
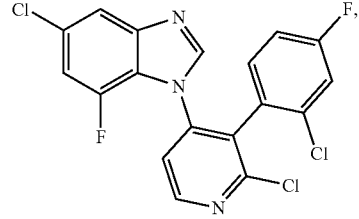

-continued

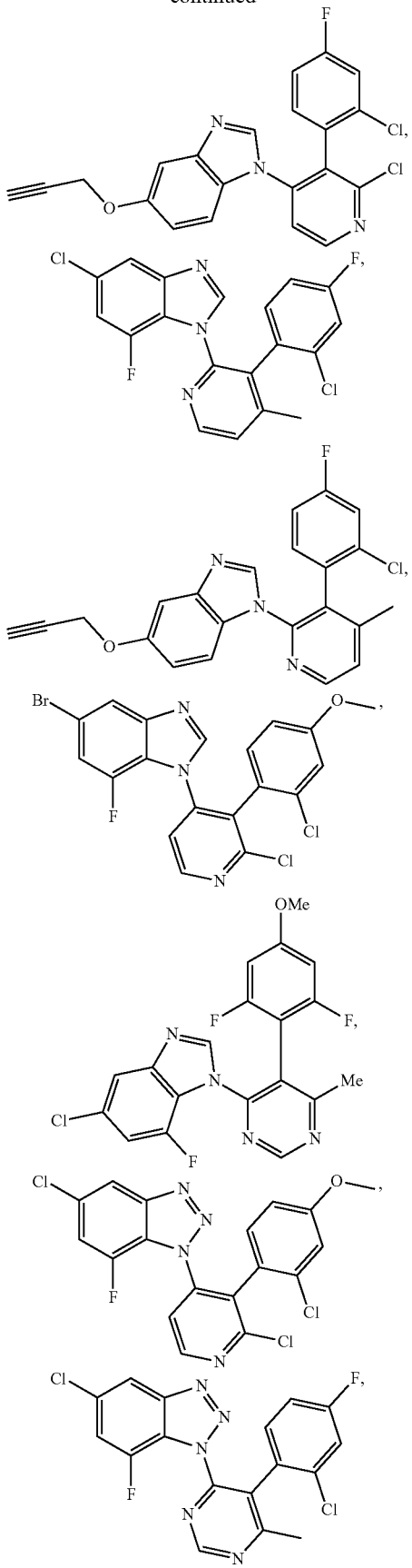

-continued

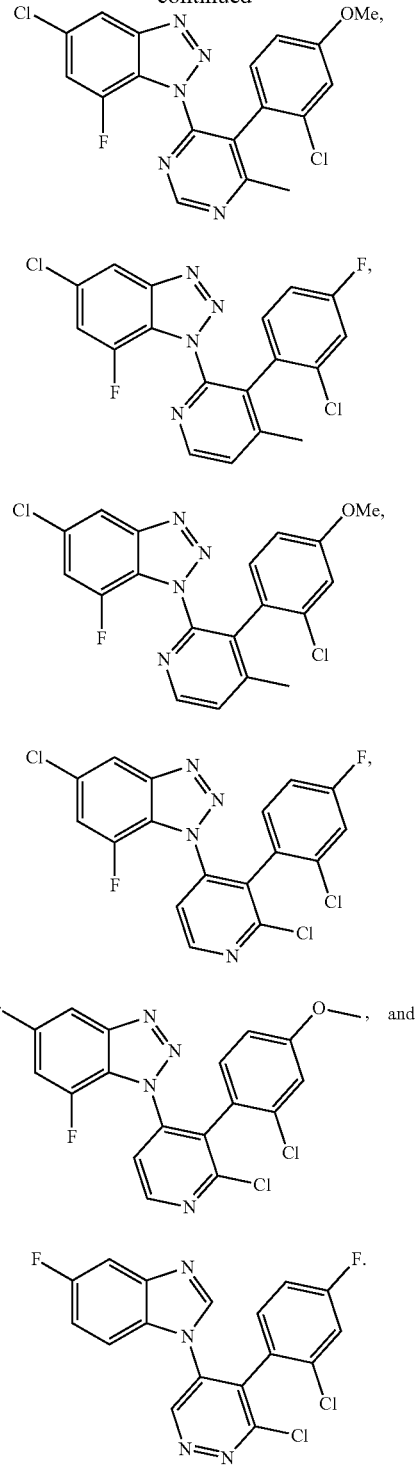

19. A method for controlling fungal diseases, the method comprising applying an agronomically effective and substantially non-phytotoxic quantity of a compound of claim 1 to seeds of plants, to plants themselves or to an area where it is intended that plants will grow.

20. A fungicidal composition comprising an effective and non-phytotoxic amount of an active compound of claim 1.

* * * * *